United States Patent
Aikawa et al.

(10) Patent No.: US 8,742,162 B2
(45) Date of Patent: Jun. 3, 2014

(54) METHOD FOR PRODUCING OPTICALLY ACTIVE 1-AMINO-2-VINYLCYCLOPROPANECARBOXYLIC ACID ESTER

(75) Inventors: Toshiaki Aikawa, Toyonaka (JP); Junichi Yasuoka, Kobe (JP); Tetsuya Ikemoto, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 112 days.

(21) Appl. No.: 13/388,575

(22) PCT Filed: Aug. 5, 2010

(86) PCT No.: PCT/JP2010/063674
§ 371 (c)(1),
(2), (4) Date: Feb. 2, 2012

(87) PCT Pub. No.: WO2011/019066
PCT Pub. Date: Feb. 17, 2011

(65) Prior Publication Data
US 2012/0130116 A1 May 24, 2012

(30) Foreign Application Priority Data
Aug. 10, 2009 (JP) ................................. 2009-185695

(51) Int. Cl.
*C07C 67/30* (2006.01)
*C07C 67/317* (2006.01)
*C07C 69/743* (2006.01)
*C07C 69/747* (2006.01)
*C07C 67/48* (2006.01)
*C07C 67/62* (2006.01)

(52) U.S. Cl.
USPC ......................................................... 560/124

(58) Field of Classification Search
None
See application file for complete search history.

(56) References Cited

U.S. PATENT DOCUMENTS

| | | |
|---|---|---|
| 2002/0037998 A1 | 3/2002 | Llinas-Brunet et al. |
| 2005/0143316 A1 | 6/2005 | Tu et al. |

FOREIGN PATENT DOCUMENTS

| | | |
|---|---|---|
| EP | 1277755 A1 | 1/2003 |

OTHER PUBLICATIONS

Database CAPLUS on STN, Acc. No. 2005:529480, Beaulieu et al., Journal of Organic Chemistry (2005), 70(15), p. 5869-5879 (abstract).*
Extended European Search Report issued Dec. 12, 2012 in EP Application No. 10808249.6.
Int'l Preliminary Report on Patentability issued Mar. 22, 2012 in Int'l Application No. PCT/JP2010/063674.
Int'l Search Report issued Sep. 7, 2010 in Int'l Application No. PCT/JP2010/063674.
Beaulieu et al, "Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease," The Journal of Organic Chemistry, vol. 70, No. 15, pp. 5869-5879 (2005).
Belyk et al, "Enantioselective Synthesis of (1R,2S)-1-Amino-2-vinylcyclopropanecarboxylic Acid Ethyl Ester (Vinyl-ACCA-OEt) by Asymmetric Phase-Transfer Catalyzed Cyclopropanation of (E)-N-Phenylmethyleneglycine Ethyl Ester," Organic Process Research & Development, vol. 14, No. 3, pp. 692-700 (2010).
Zeng et al, "Epinnerization Reaction of a Substituted Vinylcyclopropane Catalyzed by Ruthenium Carbenes: Mechanistic Analysis," The Journal of Organic Chemistry, vol. 71, No. 23, pp. 8864-8875 (2006).
OOI et al, "Practical Catalytic Enantioselective Synthesis of alpha,alpha-Dialkyl-alpha-amino Acids by Chiral Phase-Transfer Catalysis," Journal of the American Chemical Society, vol. 122, No. 21, pp. 5228-5229 (2000).

* cited by examiner

*Primary Examiner* — Brian J Davis
(74) *Attorney, Agent, or Firm* — Panitch Schwarze Belisario & Nadel LLP

(57) ABSTRACT

1-Amino-2-vinylcyclopropanecarboxylic acid ester, which is useful as a synthetic intermediate of pharmaceuticals, can be produced by a process of producing 1-amino-2-vinylcyclopropanecarboxylic acid ester represented by formula (4):

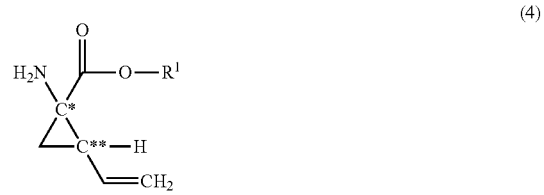

(4)

including a step of hydrolysis of an optically active 1-N-(arylmethylene)amino-2-vinylcyclopropanecarboxylic acid ester represented by formula (3):
which is obtained by reacting an N-(arylmethylene)glycine ester represented by formula (1):
with a compound represented by formula (2):
in the presence of a base and an optically active quaternary ammonium salt.

19 Claims, No Drawings

METHOD FOR PRODUCING OPTICALLY ACTIVE 1-AMINO-2-VINYLCYCLOPROPANECARBOXYLIC ACID ESTER

CROSS-REFERENCE TO RELATED APPLICATION

This application is a Section 371 of International Application No. PCT/JP2010/063674, filed Aug. 5, 2010, which was published in the Japanese language on Feb. 17, 2011, under International Publication No. WO 2011/019066 A1, and the disclosure of which is incorporated herein by reference.

TECHNICAL FIELD

The present invention relates to a method for producing an optically active 1-amino-2-vinylcyclopropanecarboxylic acid ester, and an intermediate for the production of an optically active 1-amino-2-vinylcyclopropanecarboxylic acid ester and a method for producing the same.

BACKGROUND ART

An optically active 1-amino-2-vinylcyclopropanecarboxylic acid ester is, for example, useful as an intermediate for synthesis of medicines such as an antiviral agent.

It is known that an optically active 1-amino-2-vinylcyclopropanecarboxylic acid ester is produced, for example, by reacting an N-phenylmethyleneglycine ester with (E)-1,4-dibromo-2-butene in toluene in the presence of lithium t-butoxide to obtain a 1-N-(phenylmethylene)amino-2-vinylcyclopropanecarboxylic acid ester, subjecting the obtained ester to an acid treatment to synthesize a racemic 1-amino-2-vinylcyclopropanecarboxylic acid ester, protecting an amino group of the thus synthesized 1-amino-2-vinylcyclopropanecarboxylic acid ester with a t-butoxycarbonyl group, performing an optical resolution of the ester by an enzyme reaction to remove the t-butoxycarbonyl group (see, for example, Journal of Organic Chemistry, Vol. 70, pp. 5869-5879, 2005).

However, the above-mentioned method had a problem that it is difficult to reuse an unnecessary isomer through racemization, obtained by the optical resolution of the enzyme reaction, since the 1-amino-2-vinylcyclopropanecarboxylic acid ester has two asymmetric centers.

Under these circumstances, there has been required a novel method for producing the optically active 1-amino-2-vinylcyclopropanecarboxylic acid ester.

DISCLOSURE OF THE INVENTION

The present invention provides a novel method for producing an optically active 1-amino-2-vinylcyclopropanecarboxylic acid ester.

That is, the present invention includes the followings:

[1] A method for producing an optically active 1-N-(arylmethylene)amino-2-vinylcyclopropanecarboxylic acid ester represented by formula (3)

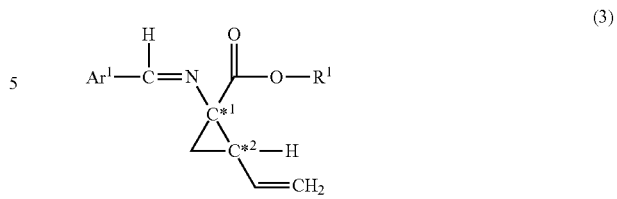

(wherein $Ar^1$ and $R^1$ are as defined below, $C^{*1}$ and $C^{*2}$ represent an asymmetric carbon atom, $C^{*2}$ is an S-configuration when $C^{*1}$ is an R-configuration, and $C^{*2}$ is an R-configuration when $C^{*1}$ is an S-configuration), which comprises a step of reacting an N-(arylmethylene)glycine ester represented by formula (1)

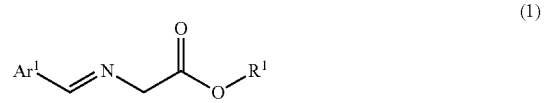

(wherein $Ar^1$ represents an aromatic group, and $R^1$ represents an alkyl group having 1 to 12 carbon atoms or an alkenyl group having 2 to 12 carbon atoms), with a compound represented by formula (2)

(wherein $Y^1$ and $Y^2$, each independently represents a halogen atom, an alkanesulfonyloxy group having 1 to 6 carbon atoms, a perfluoroalkanesulfonyloxy group having 1 to 6 carbon atoms or a benzenesulfonyloxy group, in which one or more hydrogen atoms contained in the benzenesulfonyloxy group, each independently may be substituted with an alkyl group having 1 to 6 carbon atoms, a halogen atom or a nitro group), in the presence of a base and an optically active quaternary ammonium salt.

[2] The method according to [1], wherein $Ar^1$ is a phenyl group which may be substituted with one or more selected from the group consisting of an alkyl group having 1 to 12 carbon atoms, an alkoxy group having 1 to 12 carbon atoms, a halogen atom, a nitro group, a cyano group and a trifluoromethyl group.

[3] The method according to [1], wherein $Ar^1$ is a phenyl group or a 4-chlorophenyl group.

[4] The method according to any of [1] to [3], wherein $R^1$ is an alkyl group having 1 to 12 carbon atoms.

[5] The method according to any of [1] to [4], wherein the reaction of the N-(arylmethylene)glycine ester represented by formula (1) with the compound represented by formula (2) is carried out using water and an aromatic solvent or an ether solvent.

[6] The method according to any of [1] to [5], wherein the optically active quaternary ammonium salt is a compound represented by formula (5)

(5)

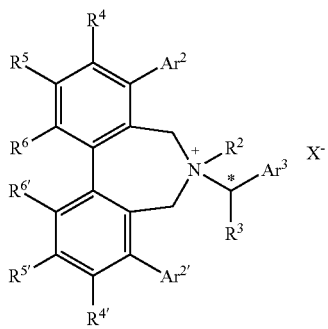

(wherein $Ar^2$ and $Ar^{2'}$, each independently represents a phenyl group which is optionally substituted, $Ar^3$ represents an optionally substituted aromatic hydrocarbon group, a straight-chain hydrocarbon group having 1 to 12 carbon atoms which is optionally substituted, or a branched or cyclic aliphatic hydrocarbon group having 3 to 12 carbon atoms which is optionally substituted, $R^2$ represents an aliphatic hydrocarbon group having 1 to 12 carbon atoms which is optionally substituted, $R^3$ represents a straight-chain hydrocarbon group having 1 to 12 carbon atoms, or $R^2$ and $R^3$ may be combined to form an alkylene group having 2 to 6 carbon atoms, $R^4$, $R^{4'}$, $R^5$, $R^{5'}$, $R^6$ and $R^{6'}$ each independently represents a hydrogen atom, an aliphatic hydrocarbon group having 1 to 12 carbon atoms or an alkoxy group having 1 to 12 carbon atoms, * represents an asymmetric carbon atom, and $X^-$ represents a monovalent anion).

[7] The method according to [6], wherein $Ar^2$ and $Ar^{2'}$, each independently represents a 3,4,5-trifluorophenyl group or a 3,5-bis(trifluoromethyl)phenyl group, $R^2$ and $R^3$, each independently represents an alkyl group having 1 to 12 carbon atoms, and $Ar^3$ represents a phenyl group or a naphthyl group.

[8] The method according to any of [1] to [5], wherein the optically active quaternary ammonium salt is a compound represented by formula (6)

(6)

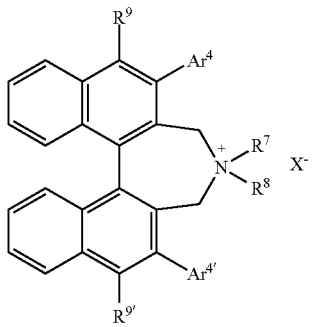

(wherein $Ar^4$ and $Ar^{4'}$, each independently represents an optionally substituted phenyl group, $R^7$ and $R^8$, each independently represents an aliphatic hydrocarbon group having 1 to 12 carbon atoms, $R^9$ and $R^{9'}$, each independently represents a hydrogen atom, an aliphatic hydrocarbon group having 1 to 12 carbon atoms or an alkoxy group having 1 to 12 carbon atoms, and $X^-$ represents a monovalent anion).

[9] An optically active 1-N-(arylmethylene)amino-2-vinylcyclopropanecarboxylic acid ester represented by formula (3)

(3)

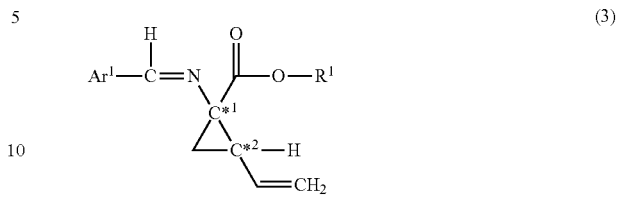

(wherein $Ar^1$ represents an aromatic group, $R^1$ represents an alkyl group having 1 to 12 carbon atoms or an alkenyl group having 2 to 12 carbon atoms, and $C^{*1}$ and $C^{*2}$ represent an asymmetric carbon atom, $C^{*2}$ is an S-configuration when $C^{*1}$ is an R-configuration, and $C^{*2}$ is an R-configuration when $C^{*1}$ is an S-configuration).

[10] The 1-N-(arylmethylene)amino-2-vinylcyclopropanecarboxylic acid ester according to [9], wherein $R^1$ is an alkyl group having 1 to 12 carbon atoms and $Ar^1$ is a phenyl group or a 4-chlorophenyl group.

[11] A method for producing an optically active 1-amino-2-vinylcyclopropanecarboxylic acid ester represented by formula (4)

(4)

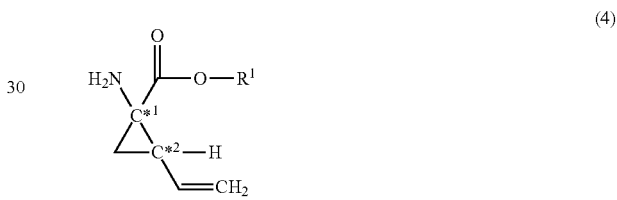

(wherein $R^1$, $C^{*1}$ and $C^{*2}$ are as defined below), which comprises a step of subjecting an optically active 1-N-(arylmethylene)amino-2-vinylcyclopropanecarboxylic acid ester represented by formula (3)

(3)

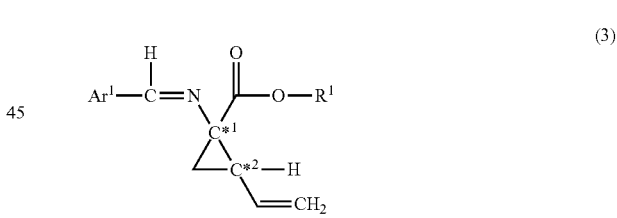

(wherein $Ar^1$ and $R^1$ are as defined below, $C^{*1}$ and $C^{*2}$ represent an asymmetric carbon atom, $C^{*2}$ is an S-configuration when $C^{*1}$ is an R-configuration, and $C^{*2}$ is an R-configuration when $C^{*1}$ is an S-configuration) to imine-hydrolysis, which is obtained by reacting an N-(arylmethylene)glycine ester represented by formula (1)

(1)

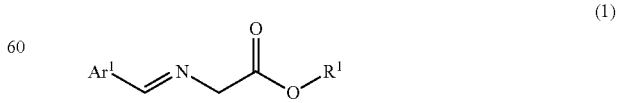

(wherein $Ar^1$ represents an aromatic group and $R^1$ represents an alkyl group having 1 to 12 carbon atoms or an alkenyl group having 2 to 12 carbon atoms), with a compound represented by formula (2)

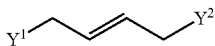

(wherein $Y^1$ and $Y^2$, each independently represents a halogen atom, an alkanesulfonyloxy group having 1 to 6 carbon atoms, a perfluoroalkanesulfonyloxy group having 1 to 6 carbon atoms or a benzenesulfonyloxy group, in which one or more hydrogen atoms contained in the benzenesulfonyloxy group, each independently may be substituted with an alkyl group having 1 to 6 carbon atoms, a halogen atom or a nitro group), in the presence of a base and an optically active quaternary ammonium salt.

[12] A method for producing an optically active 1-amino-2-vinylcyclopropanecarboxylic acid ester represented by formula (4)

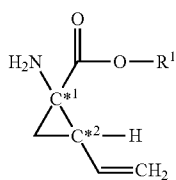

(wherein $R^1$, $C^{*1}$ and $C^{*2}$ are as defined below), which comprises steps of subjecting an optically active 1-N-(arylmethylene)amino-2-vinylcyclopropanecarboxylic acid ester represented by formula (3)

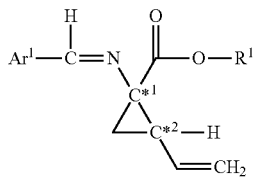

(wherein $Ar^1$ and $R^1$ are as defined below, $C^{*1}$ and $C^{*2}$ represent an asymmetric carbon atom, $C^{*2}$ is an S-configuration when $C^{*1}$ is an R-configuration, and $C^{*2}$ is an R-configuration when $C^{*1}$ is an S-configuration) to imine-hydrolysis, which is obtained by reacting an N-(arylmethylene)glycine ester represented by formula (1)

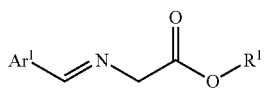

(wherein $Ar^1$ represents an aromatic group and $R^1$ represents an alkyl group having 1 to 12 carbon atoms or an alkenyl group having 2 to 12 carbon atoms), with a compound represented by formula (2)

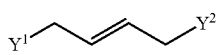

(wherein $Y^1$ and $Y^2$, each independently represents a halogen atom, an alkanesulfonyloxy group having 1 to 6 carbon atoms, a perfluoroalkanesulfonyloxy group having 1 to 6 carbon atoms or a benzenesulfonyloxy group, in which hydrogen atoms contained in the benzenesulfonyloxy group, each independently may be substituted with at least one substituent selected from the group consisting of an alkyl group having 1 to 6 carbon atoms, a halogen atom or a nitro group), in the presence of a base and an optically active quaternary ammonium salt; and forming a salt of the product obtained by the imine-hydrolysis and an achiral acid, and purifying the salt.

[13] The method according to [12], wherein the achiral acid is sulfuric acid or a halogen-substituted benzoic acid.

[14] The method according to [12], wherein the step of purifying the salt is a step of forming a salt of the product obtained by imine-hydrolysis and sulfuric acid in a solvent, precipitating a salt having a low optical purity, obtaining the salt dissolved in the solvent, isolating a 1-amino-2-vinylcyclopropanecarboxylic acid ester from the obtained salt, forming a salt of the isolated 1-amino-2-vinylcyclopropanecarboxylic acid ester and a halogen-substituted benzoic acid, and recrystallizing the salt.

[15] A method for improving an optical purity of an optically active 1-amino-2-vinylcyclopropanecarboxylic acid ester by deriving an optically active 1-amino-2-vinylcyclopropanecarboxylic acid ester represented by formula (4)

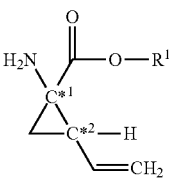

(wherein $R^1$ represents an alkyl group having 1 to 12 carbon atoms or an alkenyl group having 2 to 12 carbon atoms, $C^{*1}$ and $C^{*2}$ represent an asymmetric carbon atom, $C^{*2}$ is an S-configuration when $C^{*1}$ is an R-configuration, and $C^{*2}$ is an R-configuration when is an S-configuration), to a salt with an achiral acid, and purifying the salt.

[16] The method according to [15], wherein the achiral acid is sulfuric acid or a halogen-substituted benzoic acid.

[17] The method according to [15], which comprises forming a salt of an optically active 1-amino-2-vinylcyclopropanecarboxylic acid ester represented by formula (4) with sulfuric acid in a solvent, precipitating a salt having a low optical purity, obtaining the salt dissolved in the solvent, isolating a 1-amino-2-vinylcyclopropanecarboxylic acid ester from the obtained salt, forming a salt of the isolated 1-amino-2-vinylcyclopropanecarboxylic acid ester and a halogen-substituted benzoic acid, and recrystallizing the salt.

[18] A salt of an optically active 1-amino-2-vinylcyclopropanecarboxylic acid ester represented by formula (4)

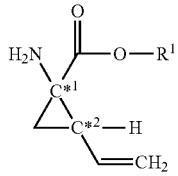 (4)

(wherein $R^1$ represents an alkyl group having 1 to 12 carbon atoms or an alkenyl group having 2 to 12 carbon atoms, $C^{*1}$ and $C^{*2}$ represent an asymmetric carbon atom, $C^{*2}$ is an S-configuration when $C^{*1}$ is an R-configuration, and $C^{*2}$ is an R-configuration when $C^{*1}$ is an S-configuration), and a halogen-substituted benzoic acid.

[19] The salt according to [18], wherein $R^1$ is an alkyl group having 1 to 12 carbon atoms and the halogen-substituted benzoic acid is 4-chlorobenzoic acid.

MODE FOR CARRYING OUT THE INVENTION

The present invention will be described in detail below.

First, an N-(arylmethylene)glycine ester represented by formula (1) (hereinafter may be referred to as glycine compound (1)) will be described.

The aromatic group represented by $Ar^1$ is a homocyclic or heterocyclic group having aromaticity which is optionally substituted. Specific examples thereof include an optionally substituted aromatic hydrocarbon group, and an optionally substituted aromatic heterocyclic group.

Examples of the aromatic hydrocarbon group include aromatic hydrocarbon groups having 6 to 14 carbon atoms such as a phenyl group, a 1-naphthyl group, a 2-naphthyl group, a 1-anthracenyl group, a 2-anthracenyl group, a 5-anthracenyl group, a 1-phenanthrenyl group, a 2-phenanthrenyl group, a 9-phenanthrenyl group, a 3,4-dihydro-1-naphthyl group, a 5,6,7,8-tetrahydro-1-naphthyl group, a 9,10-dihydro-1-anthracenyl group and a 5,6,7,8-tetrahydro-1-anthracenyl group. The aromatic hydrocarbon group may have a substituent at the substitutable position. There is no limitation on the number of the substituent, and the number of the substituent is preferably from 1 to 3. In a case of having a plurality of substituents, the substituents may be the same substituents, or may be two or more kinds of different substituents.

Examples of the substituent which may be contained in the aromatic hydrocarbon group include substituents selected from the following Group P1:
<Group P1>
an alkyl group having 1 to 12 carbon atoms,
an alkoxy group having 1 to 12 carbon atoms,
a halogen atom,
a nitro group,
a cyano group, and
a trifluoromethyl group.

In Group P1, examples of the alkyl group having 1 to 12 carbon atoms include straight-chain or branched alkyl groups having 1 to 12 carbon atoms such as a methyl group, an ethyl group, a propyl group, an isopropyl group, a butyl group, an isobutyl group, a t-butyl group, a pentyl group, a hexyl group, a heptyl group, an octyl group, a nonyl group, a decyl group, an undecyl group and a dodecyl group; and cyclic alkyl groups having 3 to 12 carbon atoms such as a cyclopropyl group, a cyclobutyl group, a cyclopentyl group, a cyclohexyl group, a cycloheptyl group and a cyclooctyl group. Examples of the alkoxy group having 1 to 12 carbon atoms include straight-chain or branched alkoxy groups having 1 to 12 carbon atoms such as a methoxy group, an ethoxy group, a propoxy group, an isopropoxy group, a butoxy group, an isobutoxy group, a t-butoxy group, a pentyloxy group, a hexyloxy group, a heptyloxy group and an octyloxy group; and cyclic alkyloxy groups having 3 to 12 carbon atoms such as a cyclopropyloxy group, a cyclobutyloxy group, a cyclopentyloxy group, a cyclohexyloxy group, a cycloheptyloxy group and a cyclooctyloxy group. Examples of the halogen atom include a fluorine atom, a chlorine atom and a bromine atom.

Examples of the optionally substituted aromatic hydrocarbon group represented by $Ar^1$ include a phenyl group, a 1-naphthyl group, a 2-naphthyl group, a 2-methylphenyl group, a 2-methoxyphenyl group, a 2-fluorophenyl group, a 2-chlorophenyl group, a 2-bromophenyl group, a 2-nitrophenyl group, a 2-cyanophenyl group, a 2-(trifluoromethyl)phenyl group, a 3-methylphenyl group, a 3-methoxyphenyl group, a 3-fluorophenyl group, a 3-chlorophenyl group, a 3-bromophenyl group, a 3-nitrophenyl group, a 3-cyanophenyl group, a 3-(trifluoromethyl)phenyl group, a 4-methylphenyl group, a 4-methoxyphenyl group, a 4-fluorophenyl group, a 4-chlorophenyl group, a 4-bromophenyl group, a 4-nitrophenyl group, a 4-cyanophenyl group, a 4-(trifluoromethyl) phenyl group, a 2,3-dichlorophenyl group, a 2,4-dichlorophenyl group, a 3,4-dichlorophenyl group and a 3,4,5-trichlorophenyl group.

Examples of the optionally substituted aromatic heterocyclic group represented by $Ar^1$ include aromatic heterocyclic groups having 3 to 13 carbon atoms such as a 2-furanyl group, a 3-furanyl group, a 2-thienyl group, a 1-pyrazolyl group, a 3-isoxazolyl group, a 3-isothiazolyl group, a 2-benzofuranyl group, a 2-benzothiophenyl group, a 3-benzopyrazolyl group, a 3-benzoisoxazolyl group, a 3-benzoisothiazolyl group, a 2-imidazolyl group, a 2-oxazolyl group, a 2-thiazolyl group, a 2-benzoimidazolyl group, a 2-benzoxazolyl group, a 2-benzothiazolyl group, a 2-pyridinyl group, a 2-quinolinyl group, a 1-isoquinolinyl group, a 3-pyridazinyl group, a 2-pyrimidyl group, a 3-cinnolinyl group, a 1-phthalazinyl group, a 2-quinazolinyl group, a 2-quinoxalinyl group, a 1-phenanthridinyl group, a 1-carbazolyl group and a 2-purinyl group. The aromatic heterocyclic group may have a substituent at the substitutable position. There is no limitation on the number of the substituent, and the number of the substituent is preferably from 1 to 3. In a case of having a plurality of substituents, the substituents may be the same substituents, or may be two or more kinds of different substituents.

Examples of the substituent which may be contained in the aromatic heterocyclic group include the same substituents as those selected from the Group P1.

Examples of the optionally substituted aromatic heterocyclic group represented by $Ar^1$ include a furanyl group, a thienyl group, a 3-methylfuran-2-yl group, a 4-methylfuran-2-yl group, a 5-methylfuran-2-yl group, a 3-methoxyfuran-2-yl group, a 4-methoxyfuran-2-yl group, a 5-methoxyfuran-2-yl group, a 3-chlorofuran-2-yl group, a chlorofuran-2-yl group and a 5-chlorofuran-2-yl group.

$Ar^1$ is preferably an optionally substituted aromatic hydrocarbon group, more preferably an optionally substituted phenyl group, still more preferably a phenyl group which may have a halogen atom(s), and yet more preferably a phenyl group or a 4-chlorophenyl group.

Examples of the alkyl group having 1 to 12 carbon atoms represented by $R^1$ include straight-chain or branched alkyl groups having 1 to 12 carbon atoms such as a methyl group, an ethyl group, a propyl group, an isopropyl group, a butyl group, an isobutyl group, a t-butyl group, a pentyl group, a hexyl group, a heptyl group, an octyl group, a nonyl group, a decyl group, an undecyl group and a dodecyl group; and cyclic alkyl groups having 3 to 12 carbon atoms such as a cyclopropyl group, a cyclobutyl group, a cyclopentyl group, a cyclohexyl group, a cycloheptyl group and a cyclooctyl group.

Examples of the alkenyl group having 2 to 12 carbon atoms represented by $R^1$ include straight-chain or branched alkenyl groups such as an ethenyl group, a 2-propenyl group, a 2-butenyl group and a 3-methyl-2-butenyl group; and cyclic alkenyl groups such as a 1-cyclohexenyl group.

$R^1$ is preferably an alkyl group having 1 to 12 carbon atoms, more preferably an ethyl group or a t-butyl group, and still more preferably an ethyl group.

Examples of the glycine compound (1) include N-phenylmethyleneglycine ethyl ester, an N-naphthalen-1-ylmethyleneglycine ethyl ester, N-naphthalene-2-ylmethyleneglycine ethyl ester, N-furan-2-ylmethyleneglycine ethyl ester, N-(4-methylphenyl)methyleneglycine ethyl ester, N-(4-methoxyphenyl)methyleneglycine ethyl ester, N-(4-fluorophenyl)methyleneglycine ethyl ester, N-(4-chlorophenyl)methyleneglycine ethyl ester, N-[4-(trifluoromethyl)phenyl]methyleneglycine ethyl ester, N-(3-chlorophenyl)methyleneglycine ethyl ester, N-(4-chlorophenyl)methyleneglycine ethyl ester, N-phenylmethyleneglycine t-butyl ester, N-(4-chlorophenyl)methyleneglycine t-butyl ester, N-phenylmethyleneglycine methyl ester and N-(4-chlorophenyl)methyleneglycine methyl ester.

The glycine compound (1) is preferably N-phenylmethyleneglycine ethyl ester, N-naphthalen-1-ylmethyleneglycine ethyl ester or N-(4-chlorophenyl)methyleneglycine ethyl ester.

The glycine compound (1) can be produced, for example, from glycine ethyl ester hydrochloride as a raw material by the method described in Journal of Organic Chemistry, Vol. 70, pp. 5869-5879, 2005. It is also possible to use commercially available products such as N-phenylmethyleneglycine ethyl ester.

Next, the compound represented by formula (2) (hereinafter may be referred to as compound (2)) will be described.

Examples of the halogen atom represented by $Y^1$ and the halogen atom represented by $Y^2$ include a chlorine atom, a bromine atom and an iodine atom. Examples of the alkanesulfonyloxy group having 1 to 6 carbon atoms include a methanesulfonyloxy group, an ethanesulfonyloxy group, a propanesulfonyloxy group, a butanesulfonyloxy group, a pentanesulfonyloxy group and a hexanesulfonyloxy group. Examples of the perfluoroalkanesulfonyloxy group having 1 to 6 carbon atoms include a trifluoromethanesulfonyloxy group, a pentafluoroethanesulfonyloxy group, a perfluoropropanesulfonyloxy group and a perfluorohexanesulfonyloxy group.

One or more hydrogen atoms in the benzenesulfonyloxy group represented by $Y^1$ and the benzenesulfonyloxy group represented by $Y^2$, each independently may be substituted from the group consisting of an alkyl group having 1 to 6 carbon atoms, a halogen atom and a nitro group. Examples of the alkyl group having 1 to 6 carbon atoms include a methyl group, an ethyl group, a propyl group, an isopropyl group, a butyl group and t-butyl. Examples of the halogen atom include a fluorine atom, a chlorine atom and a bromine atom. Examples of the benzenesulfonyloxy group having such a substituent include a 4-methylbenzenesulfonyloxy group, a 2-nitrobenzenesulfonyloxy group, a nitrobenzenesulfonyloxy group, a 4-nitrobenzenesulfonyloxy group, a 2,4-dinitrobenzenesulfonyloxy group, a 4-fluorobenzenesulfonyloxy group and a pentafluorobenzenesulfonyloxy group.

$Y^1$ and $Y^2$, each independently represents preferably a chlorine atom, a bromine atom or a methanesulfonyloxy group, and more preferably a bromine atom.

Examples of the compound (2) include (E)-1,4-dibromo-2-butene, (E)-1,4-dichloro-2-butene, (E)-1,4-dimethanesulfonyloxy-2-butene and (E)-1-bromo-4-chloro-2-butene. The compound (2) is preferably (E)-1,4-dibromo-2-butene or (E)-1,4-dichloro-2-butene, and more preferably (E)-1,4-dibromo-2-butene.

The compound (2) can be produced by a known method, and commercially available products can also be used.

Next, the optically active 1-N-(arylmethylene)amino-2-vinylcyclopropanecarboxylic acid ester represented by the formula (3) (hereinafter may be referred to as optically active compound (3)) will be descried. In the optically active compound (3), $Ar^1$ and $R^1$ have the same meaning as those of $Ar^1$ and $R^1$ in the glycine compound (1).

There is no limitation on the optical purity of the optically active compound (3), as long as one enantiomer exists excessively as compared with the other enantiomer. The optically active compound (3) is a compound which has an arylmethylideneamino group represented by —N=CH—$Ar^1$ and an ethenyl group represented by —CH=$CH_2$ on a mutually different surface side with respect to a cyclopropane ring plane.

In the optically active compound (3), there exists, as the optical isomer, an isomer having an arylmethylideneamino group and an ethenyl group on the same surface side with respect to a cyclopropane ring plane, which is represented by formula (3c)

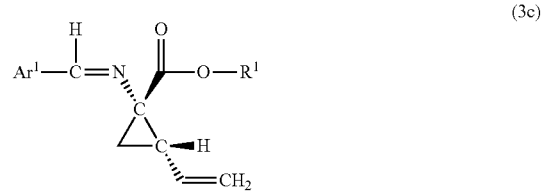

(wherein $Ar^1$ and $R^1$ are as defined above), and formula (3d)

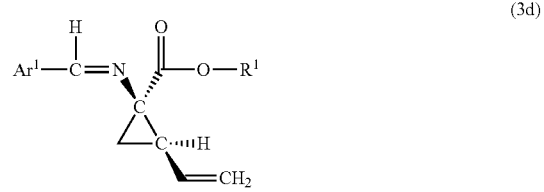

(wherein $Ar^1$ and $R^1$ are as defined above). Hereinafter, these isomers are generically referred to as diastereomer (3c-d).

Examples of the optically active compound (3) include (1S,2R)-1-(N-phenylmethylene)amino-2-vinylcyclopropanecarboxylic acid ethyl ester, (1S,2R)-1-[N-(4-chlorophenyl)methylene]amino-2-vinylcyclopropanecarboxylic acid ethyl ester, (1S,2R)-1-(N-phenylmethylene)amino-2-vinylcyclopropanecarboxylic acid t-butyl ester, (1S,2R)-1-[N-(4-chlorophenyl)methylene]amino-2-vinylcyclopropanecarboxylic acid t-butyl ester, (1S,2R)-1-(N-phenylmethylene)amino-2-vinylcyclopropanecarboxylic acid methyl ester, (1S,2R)-1-[N-(4-chlorophenyl)methylene]amino-2-vinylcyclopropanecarboxylic acid methyl ester, (1S,2R)-1-(N-naphthalen-1-ylmethylene)amino-2-vinylcyclopropanecarboxylic acid ethyl ester, (1R,2S)-1-(N-phenylmethylene)amino-2-vinylcyclopropanecarboxylic acid ethyl ester, (1R,2S)-1-[N-(4-chlorophenyl)methylene]amino-2-vinylcyclopropanecarboxylic acid ethyl ester, (1R,2S)-1-(N-phenylmethylene)amino-2-vinylcyclopropanecarboxylic acid t-butyl ester, (1R,2S)-1-[N-(4-chlorophenyl)methylene]amino-2-vinylcyclopropanecarboxylic acid t-butyl ester, (1R,2S)-1-(N-phenylmethylene)amino-2-vinylcyclopropanecarboxylic acid methyl ester, (1R,2S)-1-[N-(4-chlorophenyl)methylene]amino-2-vinylcyclopropanecarboxylic acid methyl ester and (1R,2S)-1-(N-naphthalen-1-ylmethylene)amino-2-vinylcyclopropanecarboxylic acid ethyl ester.

Next, the optically active 1-amino-2-vinylcyclopropanecarboxylic acid ester represented by formula (4) (hereinafter sometimes referred to as an optically active amino compound (4)) will be described. In the optically active amino compound (4), $R^1$ has the same meaning as that of $R^1$ in the glycine compound (1). There is no limitation on the optical purity of the optically active compound (4), as long as one enantiomer exists excessively as compared with the other enantiomer.

Examples of the optically active amino compound (4) include (1S,2R)-1-amino-2-vinylcyclopropanecarboxylic acid ethyl ester, (1S,2R)-1-amino-2-vinylcyclopropanecarboxylic acid t-butyl ester, (1S,2R)-1-amino-2-vinylcyclopropanecarboxylic acid t-butyl ester, (1S,2R)-1-amino-2-vinylcyclopropanecarboxylic acid methyl ester, (1R,2S)-1-amino-2-vinylcyclopropanecarboxylic acid ethyl ester, (1R,2S)-1-amino-2-vinylcyclopropanecarboxylic acid t-butyl ester and (1R,2S)-1-amino-2-vinylcyclopropanecarboxylic acid methyl ester.

Next, the optically active quaternary ammonium salt used in the present invention will be described.

Examples of the optically active quaternary ammonium salt include a cinchona alkaloid derivative (see, for example, Tetrahedron Letters, Vol. 40, pp. 8671-8674, 1999), a tartaric acid derivative (see, for example, Tetrahedron, Vol. 60, pp. 7743-7754, 2004) and an axial asymmetric spiro type quaternary ammonium salt (see, for example, Journal of American Chemical Society, Vol. 122, pp. 5228-5229, 2000). Examples of the preferred quaternary ammonium salt include a compound represented by formula (5) (hereinafter may be referred to as optically active quaternary ammonium salt (5)) and a compound represented by formula (6) (hereinafter may be referred to as optically active quaternary ammonium salt (6)).

In formula (5), the phenyl group in the optionally substituted phenyl group represented by $Ar^2$ and the optionally substituted phenyl group represented by $Ar^{2'}$ may have a substituent at the substitutable position. There is no limitation on the number of the substituent, and the number of the substituent is preferably from 1 to 3. In a case of having a plurality of substituents, the substituents may be the same substituents, or may be two or more kinds of different substituents.

Examples of the substituent which may be contained in the phenyl group include the same substituents as those selected from the Group P1.

Examples of the optionally substituted phenyl group represented by $Ar^2$ and the optionally substituted phenyl group represented by $Ar^{2'}$ include a phenyl group, a 2-methylphenyl group, a 3-methylphenyl group, a 4-methylphenyl group, a 3,5-dimethylphenyl group, a 3,4,5-trimethylphenyl group, a 2-t-butylphenyl group, a 3-t-butylphenyl group, a 4-t-butylphenyl group, a 2-t-butyloxyphenyl group, a 3-t-butyloxyphenyl group, a 4-t-butyloxyphenyl group, a 2-fluorophenyl group, a 3-fluorophenyl group, a 4-fluorophenyl group, a 3,5-difluorophenyl group, a 3,4,5-trifluorophenyl group, a 2-chlorophenyl group, a 3-chlorophenyl group, a 4-chlorophenyl group, a 3,5-dichlorophenyl group, a 3,4,5-trichlorophenyl group, a 2-(trifluoromethyl)phenyl group, a 3-(trifluoromethyl)phenyl group, a 4-(trifluoromethyl)phenyl group, a 3,5-bis(trifluoromethyl)phenyl group and a 3,5-difluoro-4-(trifluoromethyl)phenyl group.

$Ar^2$ and $Ar^{2'}$, each independently represents preferably a 3-fluorophenyl group, a 4-fluorophenyl group, a 3,5-difluorophenyl group, a 3,4,5-trifluorophenyl group or a 3,5-bis(trifluoromethyl)phenyl group, more preferably a 3,4,5-trifluorophenyl group or a 3,5-bis(trifluoromethyl)phenyl group, and still more preferably a 3,5-bis(trifluoromethyl)phenyl group.

In formula (5), the aromatic hydrocarbon group in the optionally substituted aromatic hydrocarbon group represented by $Ar^3$ means a cyclic hydrocarbon group having a benzene ring.

Examples of the aromatic hydrocarbon group include the same aromatic hydrocarbon groups as those in the optionally substituted aromatic hydrocarbon group represented by $Ar^1$. The aromatic hydrocarbon group may have a substituent at the substitutable position. There is no limitation on the number of the substituent, and the number of the substituent is preferably from 1 to 3. In a case of having a plurality of substituents, the substituents may be the same substituents, or may be two or more kinds of different substituents.

Examples of the substituent which may be contained in the aromatic hydrocarbon group include the same substituents as those selected from the Group P1.

Examples of the optionally substituted aromatic hydrocarbon group represented by $Ar^3$ include a phenyl group, a 1-naphthyl group, a 2-naphthyl group, a 2-methylphenyl group, a 3-methylphenyl group, a 4-methylphenyl group, a 2-methoxyphenyl group, a 3-methoxyphenyl group, a 4-methoxyphenyl group, a 2-bromophenyl group, a 3-bromophenyl group, a 4-bromophenyl group, a 2-(trifluoromethyl)phenyl group, a 3-(trifluoromethyl)phenyl group, a 4-(trifluoromethyl)phenyl group, a 2,4-dimethoxyphenyl group, a 2,4-dichlorophenyl group, a 2,4-dibromophenyl group, a 3,4-dimethoxyphenyl group, a 3,4-dibromophenyl group, a 3,5-dimethoxyphenyl group, a 3,5-dibromophenyl group and a 3,5-dibromo-4-methoxyphenyl group.

In formula (5), examples of the straight-chain hydrocarbon group having 1 to 12 carbon atoms in the optionally substituted straight-chain hydrocarbon group having 1 to 12 carbon atoms represented by $Ar^3$ include straight-chain alkyl groups having 1 to 12 carbon atoms such as a methyl group, an ethyl group, a propyl group, a butyl group, a pentyl group, a hexyl group, a heptyl group, an octyl group, a nonyl group, a decyl group, an undecyl group and a dodecyl group; straight-chain alkenyl groups having 2 to 12 carbon atoms such as an ethenyl group, a 1-propenyl group, a 2-propenyl group, a 1-butenyl group, a 1-pentenyl group, a 1-hexenyl group, a 1-heptenyl group, a 1-octenyl group and a 1-undecenyl group; and straight-chain alkynyl groups having 2 to 12 carbon atoms such as an ethynyl group, a 1-propynyl group, a 2-propynyl group, a 1-butynyl group, a 1-pentynyl group, a 1-hexynyl group, a 1-heptynyl group, a 1-octynyl and a 1-undecynyl group.

The straight-chain hydrocarbon group having 1 to 12 carbon atoms has a substituent at the substitutable position. There is no limitation on the number of the substituent, and the number of the substituent is preferably from 1 to 3. In a case of having a plurality of substituents, the substituents may be the same substituents, or may be two or more kinds of different substituents.

Examples of the substituent which may be contained in the straight-chain hydrocarbon group having 1 to 12 carbon atoms include the same substituents as those selected from the following Group P2:
<Group P2>
an alkoxy group having 1 to 12 carbon atoms,
an alkenyloxy group having 3 to 12 carbon atoms,
an alkynyloxy group having 3 to 12 carbon atoms, and
an aromatic group having 6 to 12 carbon atoms.

In Group P2, examples of the alkoxy group having 1 to 12 carbon atoms include straight-chain or branched alkoxy groups such as a methoxy group, an ethoxy group, a propoxy group, an isopropoxy group, a butoxy group, an isobutoxy group, a t-butoxy group, a pentyloxy group, a hexyloxy group, a heptyloxy group, an octyloxy group, a nonyloxy group, a decyloxy group, an undecyloxy group and a dodecyloxy group; and cyclic alkoxy groups such as a cyclopropyloxy group, a cyclobutyloxy group, a cyclopentyloxy group, a cyclohexyloxy group, a cycloheptyloxy group and a cyclooctyloxy group. Examples of the alkenyloxy group having 3 to 12 carbon atoms include a 2-propenyloxy group, a 2-butenyloxy group, a 2-methyl-2-butenyloxy group and a 3-methyl-2-butenyloxy group. Examples of the alkynyloxy group having 3 to 12 carbon atoms include a 2-propynyloxy group and a 2-butynyloxy group.

Examples of the aromatic group having 6 to 12 carbon atoms include a phenyl group, a naphthyl group, a benzofuranyl group, a benzothiophenyl group, a benzopyrazolyl group, a benzoisoxazolyl group, a benzoisothiazolyl group, a benzoimidazolyl group, a benzoxazolyl group, a benzothiazolyl group, a quinolinyl group and an isoquinolinyl group.

Herein, 1 to 3 hydrogen atoms contained in the aromatic group, each independently may be substituted with a substituent selected from the following Group P3:
<Group P3>
a saturated hydrocarbon group having 1 to 12 carbon atoms,
an aromatic group having 6 to 10 carbon atoms,
a halogen atom,
a nitro group,
a trifluoromethyl group,
a protected amino group, and
a protected hydroxyl group.

In Group P3, examples of the saturated hydrocarbon group having 1 to 12 carbon atoms include a methyl group, an ethyl group, a propyl group, an isopropyl group, a butyl group, an isobutyl group, a t-butyl group, a pentyl group, a hexyl group, a heptyl group, an octyl group, a nonyl group, a decyl group, an undecyl group, a dodecyl group, a cyclopropyl group, a cyclobutyl group, a cyclopentyl group, a cyclohexyl group, a cycloheptyl group and a cyclooctyl group. Examples of the aromatic group having 6 to 10 carbon atoms include a phenyl group, a 1-naphthyl group, a 2-naphthyl group, a 2-benzofuranyl group, a 3-benzofuranyl group, a 2-benzothiophenyl group, a 2-benzopyrazolyl group, a 3-benzoisoxazolyl group, a 3-benzoisothiazolyl group, a 2-benzoimidazolyl group, a 2-benzoxazolyl group, a 2-benzothiazolyl group, a 2-quinolinyl group and a 1-isoquinolinyl group. Examples of the halogen atom include a fluorine atom, a chlorine atom and a bromine atom. Examples of the protected amino group include a benzylamino group, a 2-methoxybenzylamino group, a 2,4-dimethoxybenzylamino group, an acetylamino group, a benzyloxycarbonylamino group, a t-butoxycarbonylamino group and an allyloxycarbonylamino group. Examples of the protected hydroxyl group include straight-chain or branched alkoxy groups having 1 to 12 carbon atoms such as a methoxy group, an ethoxy group, a propoxy group, an isopropoxy group, a butoxy group, an isobutoxy group, a t-butoxy group, a pentyloxy group, a hexyloxy group, a heptyloxy group, an octyloxy group, a nonyloxy group, a decyloxy group, an undecyloxy group and a dodecyloxy group; cyclic alkyloxy groups having 3 to 12 carbon atoms such as a cyclopropyloxy group, a cyclobutyloxy group, a cyclopentyloxy group, a cyclohexyloxy group, a cycloheptyloxy group and a cyclooctyloxy group; a methoxymethoxy group, a benzyloxy group and an acetyloxy group.

Examples of the substituted straight-chain hydrocarbon group having 1 to 12 carbon atoms represented by $Ar^3$ include a benzyl group, a diphenylmethyl group, a 1-diphenylethyl group, a 1,1-diphenyl-1-methoxymethyl group, a 1,1-diphenyl-1-(2-propenyloxy)-methyl group and a 1,1-diphenyl-1-(2-propynyloxy)-methyl group.

In formula (5), examples of the optionally substituted branched or cyclic aliphatic hydrocarbon group having 3 to 12 carbon atoms in the branched or cyclic aliphatic hydrocarbon group having 3 to 12 carbon atoms represented by $Ar^3$ include an isopropyl group, an isobutyl group, a t-butyl group, an isopentyl group, a cyclopropyl group, a cyclobutyl group, a cyclopentyl group, a cyclohexyl group, a cycloheptyl group, a cyclooctyl group, a 2-methyl-2-butenyl group and a 3-methyl-2-butenyl group.

The branched or cyclic aliphatic hydrocarbon group having 3 to 12 carbon atoms may have a substituent at the substitutable position. There is no limitation on the number of the substituent, and the number of the substituent is preferably from 1 to 3. In case of having a plurality of substituents, the substituents may be the same substituents, or may be two or more kinds of different substituents. Examples of the substituent include the same substituents as those selected from the Group P2.

Examples of the optionally substituted branched or cyclic aliphatic hydrocarbon group having 3 to 12 carbon atoms include an isopropyl group, an isobutyl group, a t-butyl group, an isopentyl group, a cyclopropyl group, a cyclobutyl group, a cyclopentyl group, a cyclohexyl group, a cycloheptyl group, a cyclooctyl group, a 2-methyl-2-butenyl group, a 3-methyl-2-butenyl group, a 1-methyl-2-phenylpropyl group, a 1-methyl-1-phenylethyl group and a 1-methyl-1-methoxyethyl group.

$Ar^3$ is preferably an optionally substituted aromatic hydrocarbon group or an optionally substituted branched or cyclic aliphatic hydrocarbon group having 3 to 12 carbon atoms, more preferably a phenyl group, a 1-naphthyl group, a 2-naphthyl group, a 3,5-dibromo-4-methoxyphenyl group, a 2,4-dichlorophenyl group or a t-butyl group, and still more preferably a phenyl group or a 1-naphthyl group.

In formula (5), examples of the optionally substituted aliphatic hydrocarbon group having 1 to 12 carbon atoms in the aliphatic hydrocarbon group having 1 to 12 carbon atoms represented by $R^2$ include straight-chain or branched alkyl groups having 1 to 12 carbon atoms such as a methyl group, an ethyl group, a propyl group, an isopropyl group, a butyl group, an isobutyl group, a t-butyl group, a pentyl group, a hexyl group, a heptyl group, an octyl group, a nonyl group, a decyl group, an undecyl group and a dodecyl group; cyclic alkyl groups having 3 to 12 carbon atoms such as a cyclopropyl group, a cyclobutyl group, a cyclopentyl group, a cyclohexyl group, a cycloheptyl group and a cyclooctyl group; alkenyl groups having 3 to 12 carbon atoms such as a 2-propenyl group, a 2-butenyl group, a 2-methyl-2-butenyl group and a 3-methyl-2-butenyl group; and alkynyl groups having 3 to 12 carbon atoms such as a 2-propynyl group and a 2-butynyl group.

The aliphatic hydrocarbon group having 1 to 12 carbon atoms may have a substituent at the substitutable position. There is no limitation on the number of the substituent, and the number of the substituent is preferably from 1 to 3. In a case of having a plurality of substituents, the substituents may be the same substituents, or may be two or more kinds of different substituents. Examples of the substituent include the same substituents as those selected from the Group P2.

$R^2$ is preferably a straight-chain or branched alkyl group having 1 to 12 carbon atoms, more preferably a straight-chain alkyl group having 1 to 8 carbon atoms, and still more preferably a methyl group.

In formula (5), examples of the straight-chain aliphatic hydrocarbon group having 1 to 12 carbon atoms represented by $R^3$ include linear alkyl groups having 1 to 12 carbon atoms such as a methyl group, an ethyl group, a propyl group, a butyl group, a pentyl group, a hexyl group, a heptyl group, an octyl group, a nonyl group, a decyl group, an undecyl group and a dodecyl group; straight-chain alkenyl groups having 2 to 12 carbon atoms such as an ethenyl group, a 1-propenyl group, a 2-propenyl group, a 1-butenyl group, a 1-pentenyl group, a 1-hexenyl group, a 1-heptenyl group, a 1-octenyl group and a 1-undecenyl group; and straight-chain alkynyl groups having 2 to 12 carbon atoms such as an ethynyl group, a 1-propynyl group, a 2-propynyl group, a 1-butynyl group, a 1-pentynyl group, a 1-hexynyl group, a 1-heptynyl group, 1-octynyl and a 1-undecynyl group.

$R^3$ is preferably a straight-chain alkyl group having 1 to 12 carbon atoms, more preferably a straight-chain alkyl group having 1 to 8 carbon atoms, and still more preferably a methyl group.

Examples of the alkylene group having 2 to 6 carbon atoms which may be formed by combination of $R^2$ and $R^3$ include a trimethylene group and a tetramethylene group.

In formula (5), examples of the aliphatic hydrocarbon group having 1 to 12 carbon atoms represented by $R^4$, the aliphatic hydrocarbon group having 1 to 12 carbon atoms represented by $R^{4'}$, the aliphatic hydrocarbon group having 1 to 12 carbon atoms represented by $R^5$, the aliphatic hydrocarbon group having 1 to 12 carbon atoms represented by $R^{5'}$, the aliphatic hydrocarbon group having 1 to 12 carbon atoms represented by $R^6$ and the aliphatic hydrocarbon group having 1 to 12 carbon atoms represented by $R^{6'}$ include the same aliphatic hydrocarbon groups having 1 to 12 carbon atoms as those described above in the optionally substituted aliphatic hydrocarbon group having 1 to 12 carbon atoms represented by $R^2$.

In formula (5), examples of the alkoxy group having 1 to 12 carbon atoms represented by $R^4$, the alkoxy group having 1 to 12 carbon atoms represented by $R^{4'}$, the alkoxy group having 1 to 12 carbon atoms represented by $R^5$, the alkoxy group having 1 to 12 carbon atoms represented by $R^{5'}$, the alkoxy group having 1 to 12 carbon atoms represented by $R^6$ and the alkoxy group having 1 to 12 carbon atoms represented by $R^{6'}$ include the same alkoxy groups having 1 to 12 carbon atoms as those in Group P2.

$R^4$ and $R^{4'}$ in formula (5), each independently represents preferably an alkoxy group having 1 to 12 carbon atoms, and more preferably a methoxy group.

$R^5$ and $R^{5'}$ in formula (5), each independently represents preferably an aliphatic hydrocarbon group having 1 to 12 carbon atoms, more preferably a straight-chain or branched alkyl group having 1 to 8 carbon atoms, and still more preferably a t-butyl group.

Both $R^6$ and $R^{6'}$ in formula (5) are preferably hydrogen atoms.

In formula (5), examples of the monovalent anion represented by $X^-$ include a hydroxide ion; halide ions such as a chloride ion, a bromide ion and an iodide ion; alkanesulfonic acid ions having 1 to 6 carbon atoms such as a methanesulfonic acid ion, an ethanesulfonic acid ion, a propanesulfonic acid ion, a butanesulfonic acid ion, a pentanesulfonic acid ion and a hexanesulfonic acid ion; and benzenesulfonic acid ions; and 1 to 3 hydrogen atoms contained in the benzenesulfonic acid, each independently may be substituted with an alkyl group having 1 to 6 carbon atoms such as a methyl group, an ethyl group, a propyl group, an isopropyl group, a butyl group, an isobutyl group, a t-butyl group, a pentyl group and a hexyl group; halogen atoms such as a fluorine atom and a chlorine atom; or a nitro group.

$X^-$ in formula (5) is preferably a halide ion, and more preferably a bromide ion.

Specific examples of the optically active quaternary ammonium salt (5) include (R)-2,10-di-t-butyl-3,9-dimethoxy-6-methyl-6-(1-naphthalen-1-ylethyl)-4,8-bis(3,5-bistrifluoromethylphenyl)-6,7-dihydro-5H-dibenzo[c,e]-azepinium bromide, (S)-2,10-di-t-butyl-3,9-dimethoxy-6-methyl-6-(1-naphthalen-1-ylethyl)-4,8-bis(3,5-bistrifluoromethylphenyl)-6,7-dihydro-5H-dibenzo[c,e]-azepinium bromide, (R)-2,10-di-t-butyl-3,9-dimethoxy-6-methyl-6-(1-phenylethyl)-4,8-bis(3,5-bistrifluoromethylphenyl)-6,7-dihydro-5H-dibenzo[c,e]-azepinium bromide, (S)-2,10-di-t-butyl-3,9-dimethoxy-6-methyl-6-(1-phenylethyl)-4,8-bis(3,5-bistrifluoromethylphenyl)-6,7-dihydro-5H-dibenzo[c,e]-azepinium bromide, (R)-2,10-di-t-butyl-3,9-dimethoxy-6-methyl-6-(1-naphthalen-1-ylethyl)-4,8-bis(3,4,5-trifluorophenyl)-6,7-dihydro-5H-dibenzo[c,e]-azepinium bromide, (S)-2,10-di-t-butyl-3,9-dimethoxy-6-methyl-6-(1-naphthalen-1-ylethyl)-4,8-bis(3,4,5-trifluorophenyl)-6,7-dihydro-5H-dibenzo[c,e]-azepinium bromide, (R)-2,10-di-t-butyl-3,9-dimethoxy-6-methyl-6-(1-phenylethyl)-4,8-bis(3,4,5-trifluorophenyl)-6,7-dihydro-5H-dibenzo[c,e]-azepinium bromide, and (S)-2,10-di-t-butyl-3,9-dimethoxy-6-methyl-6-(1-phenylethyl)-4,8-bis(3,4,5-trifluorophenyl)-6,7-dihydro-5H-dibenzo[c,e]-azepinium bromide.

The optically active quaternary ammonium salt (5) can be produced, for example, from optically active 1-naphthylethylamine as a raw material by any known method described in Tetrahedron Letters, Vol. 44, pp. 5629-5632, 2003.

In formula (6), examples of the optionally substituted phenyl group represented by $Ar^4$ and the optionally substituted phenyl group represented by $Ar^{4'}$ include the same optionally substituted phenyl group as represented by $Ar^2$ in formula (5).

$Ar^4$ and $Ar^{4'}$, each independently represents preferably a 3-fluorophenyl group, a 4-fluorophenyl group, a 3,5-difluorophenyl group, a 3,4,5-trifluorophenyl group or a 3,5-bis(trifluoromethyl)phenyl group, more preferably a 3,4,5-trifluorophenyl group or a 3,5-bis(trifluoromethyl)phenyl group, and still more preferably a 3,4,5-trifluorophenyl group.

In formula (6), examples of the aliphatic hydrocarbon group having 1 to 12 carbon atoms represented by $R^7$ and the aliphatic hydrocarbon group having 1 to 12 carbon atoms represented by $R^8$ include the same aliphatic hydrocarbon groups having 1 to 12 carbon atoms which is optionally substituted as those represented by $R^2$ in formula (5).

$R^7$ and $R^8$ in formula (6), each independently represents preferably a straight-chain or branched alkyl group having 1 to 12 carbon atoms, more preferably a straight-chain alkyl group having 1 to 8 carbon atoms, and still more preferably a butyl group.

In formula (6), examples of the aliphatic hydrocarbon group having 1 to 12 carbon atoms represented by $R^9$ and the aliphatic hydrocarbon group having 1 to 12 carbon atoms represented by $R^{9'}$ include the same aliphatic hydrocarbon groups having 1 to 12 carbon atoms which may have a substituent as those represented by $R^2$ in formula (5).

In formula (6), examples of the alkoxy group having 1 to 12 carbon atoms represented by $R^9$ and the alkoxy group having 1 to 12 carbon atoms represented by $R^{9'}$ include the same alkoxy groups having 1 to 12 carbon atoms as those in Group P2.

Both $R^9$ and $R^{9'}$ in formula (6) are preferably hydrogen atoms.

In formula (6), examples of the monovalent anion represented by $X^-$ include the same monovalent anions as those represented by $X^-$ in formula (5).

$X^-$ in formula (6) is preferably a halide ion, and more preferably a bromide ion.

Specific examples of the optically active quaternary ammonium salt (6) include (11bS)-4,4-dibutyl-4,5-dihydro-2,6-bis(3,4,5-trifluorophenyl)-3H-dinaphtho[2,1-c:1',2'-e]azepinium bromide, (11bR)-4,4-dibutyl-4,5-dihydro-2,6-bis(3,4,5-trifluorophenyl)-3H-dinaphtho[2,1-c:1',2'-e]azepinium bromide, (11bS)-4,4-dibutyl-4,5-dihydro-2,6-bis(3,5-bistrifluoromethylphenyl)-3H-dinaphtho[2,1-c:1',2'-e]azepinium bromide, and (11bR)-4,4-dibutyl-4,5-dihydro-2,6-bis(3,5-bistrifluoromethylphenyl)-3H-dinaphtho[2,1-c:1',2'-e]azepinium bromide.

The optically active quaternary ammonium salt (6) can be produced, for example, by any known method described in Angewandte Chemie International Edition, Vol. 44, pp. 1549-1551, 2005.

The optically active quaternary ammonium salt is preferably an optically active quaternary ammonium salt (5) or an optically active quaternary ammonium salt (6) from the viewpoints of obtaining the optically active compound (3) having good optical purity and suppressing the formation of the diastereomer (3c-d), and more preferably an optically active quaternary ammonium salt (5) from the viewpoints of obtaining the optically active compound (3) having better optical purity and further suppressing the formation of the diastereomer (3c-d). The optically active quaternary ammonium salt is more preferably (R)-2,10-di-t-butyl-3,9-dimethoxy-6-methyl-6-(1-naphthalen-1-ylethyl)-4,8-bis(3,5-bistrifluoromethylphenyl)-6,7-dihydro-5H-dibenzo[c,e]-azepinium bromide, (S)-2,10-di-t-butyl-3,9-dimethoxy-6-methyl-6-(1-naphthalen-1-ylethyl)-4,8-bis(3,5-bistrifluoromethylphenyl)-6,7-dihydro-5H-dibenzo[c,e]-azepinium bromide, (R)-2,10-di-t-butyl-3,9-dimethoxy-6-methyl-6-(1-phenylethyl)-4,8-bis(3,5-bistrifluoromethylphenyl)-6,7-dihydro-5H-dibenzo[c,e]-azepinium bromide and (S)-2,10-di-t-butyl-3,9-dimethoxy-6-methyl-6-(1-phenylethyl)-4,8-bis(3,5-bistrifluoromethylphenyl)-6,7-dihydro-5H-dibenzo[c,e]-azepinium bromide.

There is no limitation on the optical purity of the optically active quaternary ammonium salt, and the optical purity is preferably 90% e.e. (hereinafter, e.e. denotes enantiomeric excess) or more, more preferably 95% e.e. or more, still more preferably 98% e.e. or more, and particularly preferably 99% e.e. or more, from the viewpoint of obtaining the optically active compound (3) having a good optical purity.

Examples of the base used in the present invention include alkali metal hydroxides such as sodium hydroxide, potassium hydroxide and cesium hydroxide; alkali metal carbonic acid compounds such as potassium carbonate and sodium carbonate; and tertiary amines such as triethylamine and diisopropylethylamine.

The base is preferably an alkali metal hydroxide, and more preferably potassium hydroxide.

The method for producing an optically active compound (3) in the present invention includes a step of reacting a glycine compound (1) with a compound (2) in the presence of a base and an optically active quaternary ammonium salt. Hereinafter, the reaction of a glycine compound (1) with a compound (2) in the presence of a base and an optically active quaternary ammonium salt may be referred to as the present reaction.

The present reaction is preferably carried out in the presence of a solvent. Examples of the solvent include an aliphatic hydrocarbon solvent, an aromatic solvent, an ether solvent, an alcohol solvent, a nitrile solvent, an ester solvent, a chlorinated aliphatic hydrocarbon solvent, an aprotic polar solvent and water. These solvents may be used alone, or a mixture of two or more of these solvents may be used.

Examples of the aliphatic hydrocarbon solvent include pentane, hexane, isohexane, heptane, isoheptane, octane, isooctane, nonane, isononane, decane, isodecane, undecane, dodecane, cyclopentane, cyclohexane, methylcyclohexane, t-butylcyclohexane and petroleum ether. Examples of the aromatic solvent include benzene, toluene, ethylbenzene, isopropylbenzene, t-butylbenzene, xylene, mesitylene, monochlorobenzene, monofluorobenzene, α,α,α-trifluoromethylbenzene, 1,2-dichlorobenzene, 1,3-dichlorobenzene, 1,2,3-trichlorobenzene and 1,2,4-trichlorobenzene. Examples of the ether solvent include tetrahydrofuran, methyltetrahydrofuran, diethyl ether, dipropyl ether, diisopropyl ether, dibutyl ether, dipentyl ether, dihexyl ether, diheptyl ether, dioctyl ether, t-butyl methyl ether, cyclopentyl methyl ether, 1,2-dimethoxyethane, diethylene glycol dimethyl ether, anisole and diphenyl ether. Examples of the alcohol solvent include methanol, ethanol, 1-propanol, 2-propanol, 1-butanol, isobutyl alcohol, t-butyl alcohol, 1-pentanol, 2-pentanol, isopentyl alcohol, 1-hexanol, 2-hexanol, isohexyl alcohol, 1-heptanol, 2-heptanol, 3-heptanol, isopeptyl alcohol, ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol mono-t-butyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether and diethylene glycol mono-t-butyl ether. Examples of the nitrile solvent include acetonitrile, propionitrile and benzonitrile. Examples of the ester solvent include ethyl acetate, propyl acetate, isopropyl acetate, butyl acetate, isobutyl acetate, t-butyl acetate, amyl acetate and isoamyl acetate. Examples of the chlorinated aliphatic hydrocarbon solvent include dichloromethane, chloroform and 1,2-dichloroethane. Examples of the aprotic polar solvent include dimethyl sulfoxide, sulfolane, N,N-dimethylformamide, N,N-dimethylacetamide, N,N-dimethylpropionamide, N-methylpyrrolidone, γ-butyrolactone, dimethyl carbonate, diethyl carbonate, ethylene carbonate, propylene carbonate, 1,3-dimethyl-2-imidazolidone and 1,3-dimethyl-3,4,5,6-tetrahydro-2(1H)-pyridinone.

The solvent is preferably used as a mixture of water and the solvent other than water, more preferably a mixture of water and an aromatic solvent or an ether solvent, and still more preferably a mixture of water and toluene or t-butyl methyl ether.

In the present reaction, the use amount of the compound (2) is preferably within a range from 0.8 to 20 mol, more preferably within a range from 0.9 to 5 mol, based on 1 mol of the glycine compound (1).

In the present reaction, there is no limitation on the use amount of the optically active quaternary ammonium salt, and the use amount is preferably within a range from 0.00001 to 0.5 mol, and more preferably from 0.001 to 0.1 mol, based on 1 mol of the glycine compound (1).

In the present reaction, the use amount of the base is preferably within a range from 2 to 30 mol, and more preferably from 4 to 15 mol, based on 1 mol of the glycine compound (1).

When the present reaction is carried out in the presence of a solvent, there is no limitation on the use amount of the solvent, and the use amount is preferably within a range from 1 to 100 mL, and more preferably from 3 to 30 mL, based on 1 g of the glycine compound (1).

The reaction temperature of the present reaction is preferably selected from a range of −30 to 70° C., and more preferably −10 to 40° C.

The reaction time of the present reaction can be adjusted according to the use amount of the optically active quaternary ammonium salt, the reaction temperature and the like, and the reaction time is preferably within a range from 1 to 120 hours.

The degree of the progress of the present reaction can be confirmed, for example, by analysis means such as gas chromatography or liquid chromatography.

There is no regulation of the mixing method of reaction reagents. Examples thereof include a method of optionally mixing a glycine compound (1) with a solvent, adding a compound (2) and an optically active quaternary ammonium salt thereto, adjusting the temperature of the obtained mixture to the reaction temperature, and adding a base to the mixture adjusted to the reaction temperature.

After completion of the present reaction, the optical purity of the obtained optically active compound (3) is, for example, within a range from about 40% e.e. to about 95% e.e. when an optically active quaternary ammonium salt (5) or an optically active quaternary ammonium salt (6) is used as the optically active quaternary ammonium salt.

When the optically active compound (3) is obtained as a mixture with a diastereomer (3c-d), from the viewpoint of facilitating the purification of the optically active compound (3), it is preferred to convert the diastereomer (3c-d) into a 7-membered ring compound (hereinafter may be referred to as 7-membered ring compound (7)) represented by formula (7)

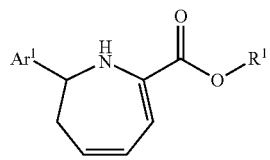

(7)

(wherein $Ar^1$ and $R^1$ are as defined above). The diastereomer (3c-d) can be converted into the 7-membered ring compound (7) under the above-mentioned conditions of the present reaction (see Non-patent Document 1). However, when the diastereomer (3c-d) is not converted into the 7-membered ring compound (7) or is insufficiently converted into the 7-membered ring compound (7), the diastereomer (3c-d) can be converted into the compound (7) by, for example, heating to about 50° C. to about 80° C. The heating time is preferably from about 1 minute to about 10 hours.

After the conversion of the diastereomer (3c-d) into the 7-membered ring compound, a ratio of the optically active compound (3) to the 7-membered ring compound (7), for example, optically active compound (3): 7-membered ring compound (7) is within a range from about 2:1 to about 40:1. When an optically active quaternary ammonium salt (5) or an optically active quaternary ammonium salt (6) is used as the optically active quaternary ammonium salt, the ratio is, for example, within a range from about 4:1 to about 40:1.

The obtained optically active compound (3) may be isolated or not. When the compound is isolated, the reaction mixture obtained after completion of the reaction may be subjected to a post-treatment such as neutralization, extraction/washing, washing with water or concentration, and may be optionally subjected to an adsorption treatment such as an activated carbon treatment, a silica treatment or an alumina treatment, and a purification treatment such as recrystallization, distillation or silica gel column chromatography. The purity and the optical purity of the optically active compound (3) may be improved, for example, by purifying the isolated optically active compound (3) through recrystallization, for example.

The thus obtained optically active compound (3) is a novel compound.

The optically active amino compound (4) is obtained by imine-hydrolysis of the optically active compound (3) obtained by the present reaction. The method for producing the optically active amino compound (4) in the present invention includes a step of subjecting the optically active compound (3) obtained by the present reaction to imine hydrolysis.

The imine-hydrolysis in the present invention means that an arylmethylideneamino group contained in the optically active compound (3) is converted into an amino group.

There is no limitation on the imine-hydrolysis, as long as it does not cause hydrolysis of an ester moiety contained in the optically active compound (3), and the imine-hydrolysis is preferably carried out by mixing the optically active compound (3) with an acid.

Examples of the acid used for the imine-hydrolysis include inorganic acids such as hydrochloric acid, sulfuric acid, phosphoric acid, nitric acid and perchloric acid; aromatic sulfonic acids such as paratoluenesulfonic acid and benzenesulfonic acid; aliphatic sulfonic acids such as methanesulfonic acid and camphorsulfonic acid; aliphatic carboxylic acids such as acetic acid, propionic acid, tartaric acid, citric acid, malic acid, succinic acid, lactic acid, maleic acid and fumaric acid; and aromatic carboxylic acids such as phthalic acid, benzoic acid, 4-nitrobenzoic acid and 4-chlorobenzoic acid.

The acid may be alone, or may be a mixture with the below-mentioned solvent.

The acid is preferably an inorganic acid, and more preferably hydrochloric acid. When hydrochloric acid is used as the acid, the concentration may be appropriately adjusted by mixing with water.

In the imine-hydrolysis, the use amount of the acid is preferably adjusted so that the mixture obtained after mixing with the acid has a pH within a range from 0 to 4. In order to adjust the pH within the above range, when the acid is hydrochloric acid, the acid may be used in an amount of 0.8 to 1.5 mol based on 1 mol of the optically active compound (3).

The imine-hydrolysis is preferably carried out in the presence of a solvent. Examples of the solvent used in the imine-hydrolysis include the same solvents as those described above used in the present reaction.

The solvent may be alone, or may be a mixture of two or more kinds of solvents.

The solvent is preferably water, an aromatic solvent or an ether solvent.

The use amount of the solvent is preferably within a range from 1 to 100 mL, and more preferably from 3 to 30 mL, based on 1 g of the optically active compound (3).

The temperature, at which the imine-hydrolysis is carried out, is, for example, selected from a range of 0 to 80° C., preferably 5 to 60° C., and more preferably 10 to 40° C.

The time, during which the imine-hydrolysis is carried out, can be adjusted according to the kind and concentration of the acid to be used, and the temperature at which the imine-hydrolysis is carried out, and is preferably within a range from 1 minute to 20 hours, and more preferably from 10 minutes to 10 hours.

There is no limitation on the mixing method in the imine-hydrolysis, and examples of the method include a method in which an optically active compound (3) is mixed with a solvent and an acid is added to the obtained mixture.

After completion of the imine-hydrolysis, the optical purity of the obtained optically active amino compound (4) is nearly equivalent to the optical purity of the optically active compound (3) subjected to the imine hydrolysis. That is, when the optically active quaternary ammonium salt (5) or the optically active quaternary ammonium salt (6) is used as the optically active quaternary ammonium salt in the present reaction, the optical purity of the obtained optically active amino compound (4) is, for example, within a range from about 40% e.e. to about 95% e.e.

The obtained optically active amino compound (4) may be isolated or not. When the compound is isolated, the reaction mixture obtained after the imine-hydrolysis may be subjected to a post-treatment such as neutralization, extraction/washing, washing with water or concentration, and may be optionally subjected to an adsorption treatment such as an activated carbon treatment, a silica treatment or an alumina treatment, and a purification treatment such as distillation or silica gel column chromatography.

The optically active amino compound (4) may be, for example, a salt with an acid capable of forming a salt with the optically active amino compound (4). Examples of the acid capable of forming a salt with the optically active amino compound (4) include acids which can be used in the above-mentioned hydrolysis. The acid is preferably an inorganic acid, and more preferably hydrochloric acid or sulfuric acid.

The method for producing an optically active amino compound (4) in the present invention preferably includes a step of forming a salt of a product obtained by imine-hydrolysis of an optically active compound (3), and an achiral acid, and purifying the salt. The optical purity of the optically active compound (4) can be improved by forming the salt. Hereinafter, the step of purifying the salt my be referred to as the purification step.

When the optical purity of the optically active amino compound (4) before subjecting to the purification step is within a range from about 40% e.e. to about 95% e.e., the optical purity of the optically active amino compound (4) obtained after the purification step is, for example, within a range from about 80% e.e. to about 100% e.e.

Examples of the achiral acid used in the purification step include sulfuric acid and a halogen-substituted benzoic acid.

Examples of the halogen-substituted benzoic acid include benzoic acid, 2-iodobenzoic acid, 3-iodobenzoic acid, 4-iodobenzoic acid, 2-chlorobenzoic acid, 3-chlorobenzoic acid, 4-chlorobenzoic acid, 2-bromobenzoic acid, 3-bromobenzoic acid, 4-bromobenzoic acid, 2,4-dichlorobenzoic acid, 3,5-dichlorobenzoic acid and 4-chloro-3-iodobenzoic acid.

The achiral acid used in the purification step is preferably sulfuric acid or 4-chlorobenzoic acid.

The use amount of the achiral acid is preferably within a range from 0.3 to 2.0 mol, and more preferably from 0.4 to 1.5 mol, based on 1 mol of the optically active compound (3). When the achiral acid is sulfuric acid, the use amount of the achiral acid is particularly preferably within a range from 0.4 to 0.6 mol based on 1 mol of the optically active compound (3). When the achiral acid is a halogen-substituted benzoic acid, the use amount of the achiral acid is particularly preferably within a range from 0.8 to 1.2 mol based on 1 mol of the optically active compound (3).

The purification step can be carried out, for example, by the method described in any one of the following methods 1 to 5:

Method 1: A salt of the product obtained by imine-hydrolysis of an optically active compound (3), and sulfuric acid is formed in a solvent and a salt having a low optical purity is precipitated, and then the salt dissolved in the solvent is recovered;

Method 2: A salt of the product obtained by imine-hydrolysis of an optically active compound (3), and a halogen-substituted benzoic acid is formed, and the salt is recrystallized;

Method 3: A salt of the product obtained by imine-hydrolysis of an optically active compound (3), and sulfuric acid is formed in a solvent and a salt having a low optical purity is precipitated, and then the salt dissolved in the solvent is obtained and a 1-amino-2-vinylcyclopropanecarboxylic acid ester is isolated from the obtained salt. A salt of the isolated 1-amino-2-vinylcyclopropanecarboxylic acid ester and a halogen-substituted benzoic acid is formed and the salt is recrystallized;

Method 4: A salt of the product obtained by imine-hydrolysis of an optically active compound (3), and a halogen-substituted benzoic acid is formed and the salt is recrystallized, and then a 1-amino-2-vinylcyclopropanecarboxylic acid ester is isolated from the salt obtained by recrystallization. A salt of the isolated 1-amino-2-vinylcyclopropanecarboxylic acid ester and sulfuric acid is formed in a solvent and a salt having a low optical purity is precipitated, and then the salt dissolved in the solvent is obtained; and Method 5: A salt of the product obtained by imine hydrolysis of an optically active compound (3), and sulfuric acid is formed in a solvent and a salt having a low optical purity is precipitated, and then the salt dissolved in the solvent was obtained and then a 1-amino-2-vinylcyclopropanecarboxylic acid ester is isolated from the obtained salt. A salt of the isolated 1-amino-2-vinylcyclopropanecarboxylic acid ester and a halogen-substituted benzoic acid is formed, and the salt is recrystallization and then a 1-amino-2-vinylcyclopropanecarboxylic acid ester is isolated from the salt obtained by recrystallization. Furthermore, a salt of the isolated 1-amino-2-vinylcyclopropanecarboxylic acid ester and sulfuric acid is formed and a salt having a low optical purity is precipitated, and then the salt dissolved in the solvent is obtained.

The purification step is preferably carried out by the method described in any of the above methods 3 to 5, and more preferably the method described in the above method 3.

Examples of the solvent used in the method 1 include the same aromatic solvent, ether solvent and alcohol solvent as those used in the present reaction. The solvent may be alone, or may be a mixed solvent of two or more kinds of these solvents.

The solvent is preferably at least one kind of a solvent selected from the group consisting of an aromatic solvent and an alcohol solvent, more preferably a mixed solvent of an aromatic solvent and an alcohol solvent, and still more preferably a mixed solvent of toluene and ethanol.

The use amount of the solvent is preferably from 1 to 100 mL, and more preferably from 3 to 30 mL, based on 1 g of the optically active compound (3).

A mixing ratio (weight ratio) in the mixed solvent of the aromatic solvent and the alcohol solvent, for example, aromatic solvent:alcohol solvent is from 2:1 to 20:1, and preferably from 4:1 to 12:1.

In the method 1, the temperature, at which a salt having a low optical purity is precipitated, is preferably selected from a range of −10 to 60° C., and more preferably a range of 10 to 40° C.

In the method 2, examples of the solvent used in recrystallization include the same aromatic solvent, ether solvent and alcohol solvent as those used in the present reaction. The solvent may be alone, or may be a mixed solvent of two or more kinds of these solvents.

The solvent used in recrystallization is preferably at least one kind of a solvent selected from the group consisting of an aromatic solvent and an ether solvent, more preferably an aromatic solvent, and still more preferably toluene.

The amount of the solvent used in recrystallization is preferably from 1 to 100 mL, and more preferably from 3 to 30 mL, based on 1 g of the optically active compound (3).

The recrystallization in the method 2 is preferably carried out by cooling crystallization or concentration crystallization.

In the method 2, the recrystallization can be preferably carried out under the conditions selected from a range from −20 to 60° C., and more preferably from −10 to 30° C.

It becomes possible to obtain an optically active amino compound (4) having a high optical purity by recrystallizing a salt of a product obtained by imine-hydrolysis of an optically active compound (3), and a halogen-substituted benzoic acid, that is, a salt of the optically active amino compound (4) and a halogen-substituted benzoic acid in the method 2.

EXAMPLES

The present invention will be described in more detail below by way of Examples.

Synthesis Example 1

Production of (E)-N-phenylmethyleneglycine ethyl ester

Glycine ethyl ester hydrochloride (69.1 g, 495 mmol) and toluene (215 g) were mixed, and N-methylpyrrolidone (32.5 g) was poured into the mixture at room temperature. Benzaldehyde (50.0 g, 471 mmol) was added dropwise to the obtained mixture, and then trimethyl orthoformate (52.5 g, 495 mmol) was added dropwise. After completion of the dropwise addition, the temperature of the obtained mixture was adjusted to 7° C. and a mixed solution of triethylamine (52.4 g, 518 mmol) and toluene (26.5 g) was added dropwise over 3 hours. After completion of the dropwise addition, the mixture was stirred at a temperature in a range from 7° C. to room temperature for 6 hours. After completion of the reaction, the reaction mixture was cooled to 5° C. and water (140 mL) was added dropwise thereto. Thereafter, stirring was stopped to perform liquid separation and then the obtained organic layer was washed with 20% brine (95 g). The obtained organic layer was dried over magnesium sulfate and the solvent was distilled off under reduced pressure to obtain a toluene solution (104.5 g) of (E)-N-phenylmethyleneglycine ethyl ester (86.9 g of pure (E)-N-phenylmethyleneglycine ethyl ester). Yield: 96%.

Synthesis Example 2

Production of (E)-N-(4-chlorophenyl)methyleneglycine ethyl ester

In the same manner as in Synthesis Example 1, except that p-chlorobenzaldehyde was used in place of benzaldehyde, a toluene solution of (E)-N-(4-chlorophenyl)methyleneglycine ethyl ester was obtained. Yield: 99%.

Synthesis Example 3

Production of (E)-N-phenylmethyleneglycine t-butyl ester

In the same manner as in Synthesis Example 1, except that glycine t-butyl ester hydrochloride was used in place of glycine ethyl ester hydrochloride and the use amount of triethylamine was changed from 1.1 mol to 1.3 mol based on 1 mol of benzaldehyde, a toluene solution of (E)-N-phenylmethyleneglycine t-butyl ester. Yield: 96%.

Synthesis Example 4

Production of (E)-N-(4-chlorophenyl)methyleneglycine t-butyl ester

In the same manner as in Synthesis Example 3, except that p-chlorobenzaldehyde was used in place of benzaldehyde, a toluene solution of (E)-N-(4-chlorophenyl)methyleneglycine t-butyl ester was obtained. Yield: 96%.

Example 1

Production of (1S,2R)-1-(N-phenylmethylene)amino-2-vinylcyclopropanecarboxylic acid ethyl ester The toluene solution (0.59 g) of the (E)-N-phenylmethyleneglycine ethyl ester (pure (E)-N-phenylmethyleneglycine ethyl ester: 0.49 g, 2.57 mmol) obtained in Synthesis Example 1 and toluene (5 mL) were mixed, and (E)-1,4-dibromo-2-butene (0.50 g, 2.34 mmol) and (R)-2,10-di-t-butyl-3,9-dimethoxy-6-methyl-6-(1-naphthalen-1-ylethyl)-4,8-bis(3,5-bistrifluoromethylphenyl)-6,7-dihydro-5H-dibenzo[c,e]-azepinium bromide (0.024 g, 0.023 mmol) were added thereto at room temperature. The obtained mixture was cooled to 0° C. and an aqueous 50% potassium hydroxide solution (1.31 g) (potassium hydroxide: 11.7 mmol) was added dropwise thereto, followed by stirring at 0° C. thereby reacting (E)-N-phenylmethyleneglycine ethyl ester with (E)-1,4-dibromo-2-butene. The reaction time was 21 hours. After completion of the reaction, water (2 mL) was added to the obtained mixture and stirring was stopped to perform liquid separation. The obtained organic layer was washed with an aqueous 10% ammonium chloride solution (2 mL). After liquid separation, the organic layer containing the titled compound, (1S,2R)-1-(N-phenylmethylene)amino-2-vinylcyclopropanecarboxylic acid ethyl ester, was obtained.

(1S,2R)-1-(N-phenylmethylene)amino-2-vinylcyclopropanecarboxylic acid ethyl ester contained in the obtained organic layer was subjected to quantitative analysis under the following conditions of high-performance liquid chromatography and a yield was calculated. Yield: 55%.

From the above analysis results, a ratio of the (1S,2R)-1-(N-phenylmethylene)amino-2-vinylcyclopropanecarboxylic acid ethyl ester to ethyl 7-phenyl-6,7-dihydro-1H-azepine-2-carboxylate as the 7-membered ring compound (7) was calculated. (1S,2R)-1-(N-phenylmethylene)amino-2-vinylcyclopropanecarboxylic acid ethyl ester:ethyl 7-phenyl-6,7-dihydro-1H-azepine-2-carboxylate=9:1.

A diastereomer of (1S,2R)-1-(N-phenylmethylene)amino-2-vinylcyclopropanecarboxylic acid ethyl ester was not detected.

<Conditions of High-Performance Liquid Chromatography Analysis>

Column: YMC Pack ODS-A-302 (measuring 4.6×150 mm, 5 μm)

Mobile phase: A=aqueous 40 mM $KH_2PO_4$ (pH 3.5—$H_3PO_4$), B=methanol, A/B=10% (0 minute)→10% (5 minutes)→70% (25 minutes)→70% (45 minutes)

Flow rate: 1.0 mL/minute

Detector: wavelength of 220 nm

Retention time: 11.7 minutes ((1S,2R)-1-(N-phenylmethylene)amino-2-vinylcyclopropanecarboxylic acid ethyl ester), 31.2 minutes (ethyl 7-phenyl-6,7-dihydro-1H-azepine-2-carboxylate)<

<Determination of Optical Purity>

Subsequently, an aqueous 1M hydrochloric acid (2 mL) was added to the obtained organic layer and a hydrolysis reaction was carried out by stirring at room temperature for 2 hours. After completion of the reaction, liquid separation was carried out and the obtained organic layer was extracted by adding water (2 mL). The obtained aqueous layers were combined to obtain (1S,2R)-1-amino-2-vinylcyclopropanecarboxylic acid ethyl ester hydrochloride as an aqueous solution. The optical purity was determined by analyzing the obtained aqueous solution under the following conditions of optical purity analysis. Optical purity: 73% e.e.

<Optical Purity Analysis Conditions>

Column: CHIRALCEL (registered trademark of Daicel Chemical Industries, Ltd.) AD-RH (measuring 4.6×150 mm, 5 μm)

Mobile phase: A=0.1% diethylamine-water, B=0.1% diethylamine-methanol, A/B=60/40

Flow rate: 0.7 mL/minute

Detector: wavelength of 215 nm

Retention time: (1R,2S) isomer=6.7 minutes, (1S,2R) isomer=10.8 minutes

Examples 2 to 7

With the exception of the conditions shown in Table 1, an optically active compound (3) was obtained in the same manner as in Example 1. The results are shown in Table 2. The use amount in Table 1 denotes the use amount of the base based on 1 mol of the glycine compound (1).

A diastereomer (3c-d) of the optically active compound (3) was not detected from the organic layer containing the optically active compound (3).

TABLE 1

| | Glycine compound (1) | Base (use amount) | Reaction temperature/ Reaction time |
|---|---|---|---|
| Example 2 | 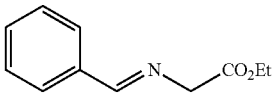 [SMILES: CCOC(=O)C/N=C/c1ccccc1] | Aqueous 50% potassium hydroxide solution (4.5 mol) | Room temperature/12 hours |
| Example 3 | 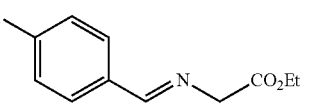 | Aqueous 50% potassium hydroxide solution (4.5 mol) | 0° C./20 hours |
| Example 4 | 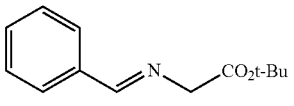 [SMILES: CC(C)(C)OC(=O)C/N=C/c1ccccc1] | Aqueous 50% potassium hydroxide solution (5.5 mol) | 0° C./36 hours, followed by room temperature/19 hours |
| Example 5 | 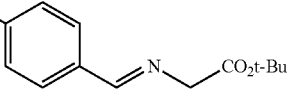 | Aqueous 50% potassium hydroxide solution (6.4 mol) | 0 to 10° C./25 hours |
| Example 6 | 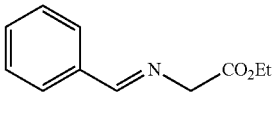 [SMILES: CCOC(=O)C/N=C/c1ccccc1] | Potassium hydroxide (2.7 mol) | 0° C./20 hours |
| Example 7 | 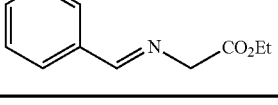 | Cesium hydroxide monohydrate (2.7 mol) | 0° C./20 hours |

TABLE 2

| | Optically active compound (3) | Yield | Optical purity | Optically active compound (3): 7-membered ring compound (7) |
|---|---|---|---|---|
| Example 2 | (benzylidene-N, CO₂Et, vinyl cyclopropane) | 48% | 48% e.e. | 9.1:1 |
| Example 3 | (4-chlorobenzylidene-N, CO₂Et, vinyl cyclopropane) | 48% | 70% e.e. | 11:1 |
| Example 4 | (benzylidene-N, CO₂t-Bu, vinyl cyclopropane) | 56% | 54% e.e. | 12:1 |
| Example 5 | (4-chlorobenzylidene-N, CO₂t-Bu, vinyl cyclopropane) | 46% | 53% e.e. | Unmeasured |
| Example 6 | (benzylidene-N, CO₂Et, vinyl cyclopropane) | 58% | 67% e.e. | 9.3:1 |
| Example 7 | (benzylidene-N, CO₂Et, vinyl cyclopropane) | 57% | 67% e.e. | 9.7:1 |

(1S,2R)-1-(N-phenylmethylene)amino-2-vinylcyclopropanecarboxylic acid ethyl ester $^1$H-NMR (CDCl$_3$, 400 MHz) δ ppm: 8.36 (1H, S), 7.77-7.73 (2H, m), 7.44-7.39 (3H, m), 5.81-5.72 (1H, m), 5.27 (1H, dd, J=1.5, 17.1 Hz), 5.12 (1H, dd, J=1.5, 10.3 Hz), 4.24 (2H, q, J=6.8 Hz), 2.30-2.23 (1H, m), 2.00 (1H, dd, J=5.4, 7.8 Hz), 1.70 (1H, dd, J=5.6, 9.3 Hz), 1.30 (3H, t, J=6.8 Hz)

(1S,2R)-1-[N-(4-chlorophenyl)methylene]amino-2-vinylcyclopropanecarboxylic acid ethyl ester $^1$H-NMR (CDCl$_3$, 400 MHz) δ ppm: 8.33 (1H, S), 7.68 (1H, d, J=8.3 Hz), 7.38 (1H, d, J=8.3 HZ), 5.81-5.72 (1H, m), 5.37 (1H, dd, J=1.5, 17.1 Hz), 5.12 (1H, dd, J=1.5, 10.3 Hz), 4.24 (2H, q, J=6.8 Hz), 2.30-2.23 (1H, m), 2.01 (1H, dd, J=5.4, 7.8 Hz), 1.70 (1H, dd, J=5.4, 9.3 Hz), 1.30 (3H, t, J=6.8 Hz)

(1S,2R)-1-(N-phenylmethylene)amino-2-vinylcyclopropanecarboxylic acid t-butyl ester ¹H-NMR (CDCl₃, 400 MHz) δ ppm: 8.39 (1H, S), 7.79-7.71 (2H, m), 7.43-7.36 (3H, m), 5.83-5.73 (1H, m), 5.27 (1H, dd, J=1.5, 17.1 Hz), 5.11 (1H, dd, J=1.5, 10.3 Hz), 2.28-2.20 (1H, m), 1.92 (1H, dd, J=5.4, 8.8 Hz), 1.61 (1H, dd, J=5.4, 9.3 Hz), 1.50 (9H, s)

(1S,2R)-1-[N-(4-chlorophenyl)methylene]amino-2-vinylcyclopropanecarboxylic acid t-butyl ester ¹H-NMR (CDCl₃, 400 MHz) δ ppm: ¹H-NMR (CD₃OD-d₄, 400 MHz) 5 ppm: 8.36 (1H, S), 7.68 (1H, d, J=8.3 Hz), 7.38 (1H, d, J=8.3 HZ), 5.81-5.71 (1H, m), 5.26 (2H, dd, J=1.5, 17.1 Hz), 5.12 (2H, dd, J=1.5, 10.3 Hz), 2.28-2.20 (1H, m), 1.94 (1H, dd, J=5.4, 7.8 Hz), 1.62 (1H, dd, J=5.4, 9.4 Hz), 1.50 (9H, s)

Examples 8 to 20

With the exception of the conditions shown in Tables 3 and 4, an optically active compound (3) was obtained in the same manner as in Example 1. The results are shown in Tables 6 and 7. The use amount in Tables 3 and 4 denotes the use amount of the optically active quaternary ammonium salt or base based on 1 mol of the glycine compound (1).

A diastereomer (3c-d) of the optically active compound (3) was not detected from the organic layer containing the optically active compound (3).

Reference Examples 1 to 3

With the exception of the conditions shown in Table 5, an optically active compound (3) was obtained in the same manner as in Example 1. The results are shown in Table 8. The use amount in Table 5 denotes the use amount of the quaternary ammonium salt or base based on 1 mol of the glycine compound (1).

A diastereomer (3c-d) of the optically active compound (3) was not detected from the organic layer containing the optically active compound (3).

TABLE 3

| | Quaternary ammonium salt (use amount) | Base (use amount) | Reaction temperature/Reaction time |
|---|---|---|---|
| Example 8 | 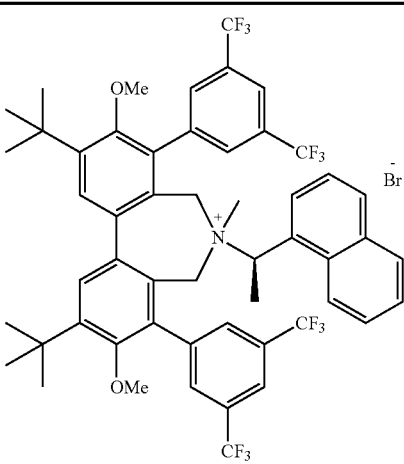<br>(0.01 mol) | Aqueous 50% potassium hydroxide solution (9.1 mol) | 0° C./8 hours |
| Example 9 | 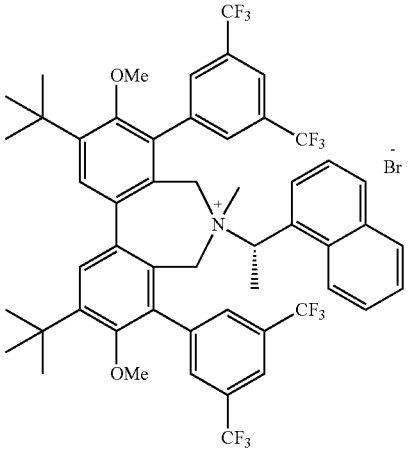<br>(0.01 mol) | Aqueous 50% potassium hydroxide solution (9.1 mol) | 0° C./14 hours |

TABLE 3-continued

| | Quaternary ammonium salt (use amount) | Base (use amount) | Reaction temperature/Reaction time |
|---|---|---|---|
| Example 10 | (0.01 mol) | Aqueous 50% potassium hydroxide solution (9.1 mol) | 0° C./16 hours |
| Example 11 | (0.005 mol) | Aqueous 50% potassium hydroxide solution (9.1 mol) | 0° C./24 hours |
| Example 12 | (0.002 mol) | Aqueous 50% potassium hydroxide solution (9.1 mol) | 0° C./32 hours |

TABLE 4

| | Quaternary ammonium salt (use amount) | Base (use amount) | Reaction temperature/Reaction time |
|---|---|---|---|
| Example 13 | (structure shown) (0.001 mol) | Aqueous 50% potassium hydroxide solution (9.1 mol) | 0° C./36 hours |
| Example 14 | (structure shown) (0.01 mol) | Aqueous 50% potassium hydroxide solution (4.5 mol) | 0° C./24 hours |
| Example 15 | (structure shown) (0.01 mol) | Aqueous 50% potassium hydroxide solution (4.5 mol) | 0° C./48 hours |

TABLE 4-continued
| | Quaternary ammonium salt (use amount) | Base (use amount) | Reaction temperature/Reaction time |
|---|---|---|---|
| Example 16 | 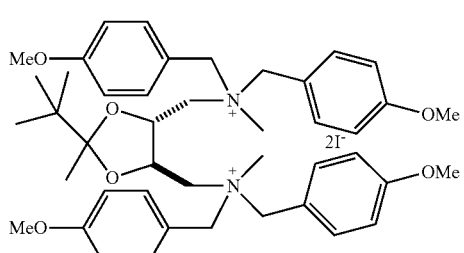 (0.01 mol) | Aqueous 50% potassium hydroxide solution (4.5 mol) | 0° C./21 hours, followed by room temperature/6 hours |
| Example 17 | 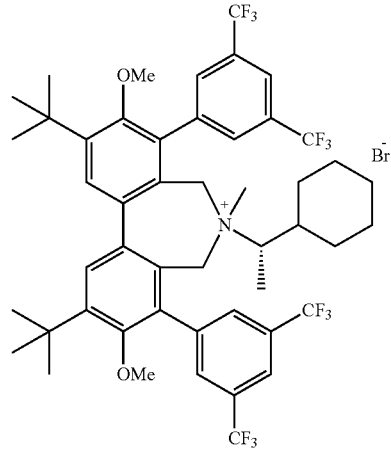 (0.003 mol) | Aqueous 50% potassium hydroxide solution (9.1 mol) | 0° C./24 hours |
| Example 18 | 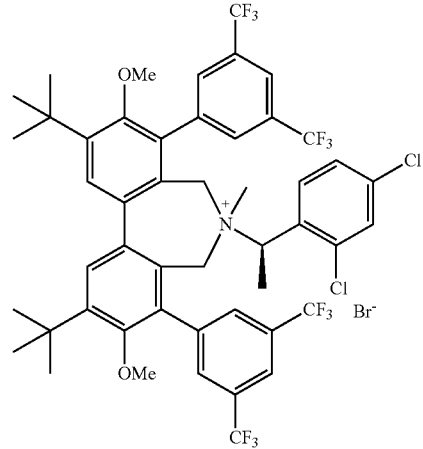 (0.003 mol) | Aqueous 50% potassium hydroxide solution (9.1 mol-fold) | 0° C./24 hours |

TABLE 4-continued

| | Quaternary ammonium salt (use amount) | Base (use amount) | Reaction temperature/Reaction time |
|---|---|---|---|
| Example 19 | 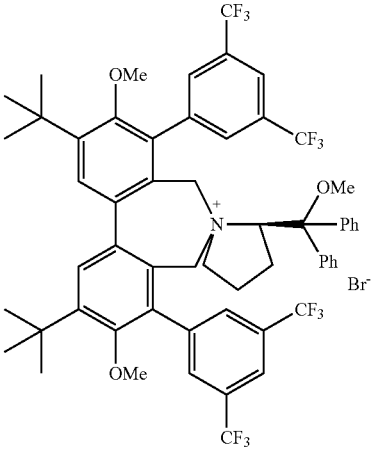 (0.01 mol) | Aqueous 50% potassium hydroxide solution (9.1 mol) | 0° C./20 hours |
| Example 20 | 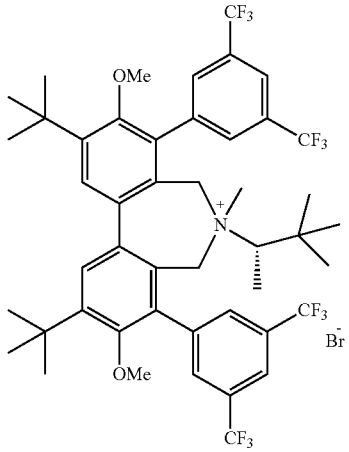 (0.005 mol) | Aqueous 50% potassium hydroxide solution (9.1 mol) | 0° C./21 hours |

TABLE 5

| | Quaternary ammonium salt (use amount) | Base (use amount) | Reaction temperature/ Reaction time |
|---|---|---|---|
| Reference Examples 1 | Tetrabutylammonium bromide (0.001 mol) | Aqueous 50% potassium hydroxide solution (4.5 mol) | 0° C., followed by room temperature/ 5 hours |
| Reference Examples 2 | Benzyltriethylammonium chloride (0.1 mol) | Aqueous 50% potassium hydroxide solution (5.5 mol) | 0° C., followed by room temperature/ 17 hours |
| Reference Examples 3 | Benzyltriethylammonium chloride (0.03 mol) | Potassium hydroxide (2.7 mol) | 0° C. |

TABLE 6

| | Optically active compound (3) | Yield | Optical purity | Optically active compound (3): 7-membered ring compound (7) |
|---|---|---|---|---|
| Example 8 | phenyl-CH=N, CO$_2$Et, vinyl cyclopropane | 59% | 74% e.e. | 10:1 |
| Example 9 | phenyl-CH=N, CO$_2$Et, vinyl cyclopropane | 61% | 73% e.e. | 11:1 |
| Example 10 | phenyl-CH=N, CO$_2$Et, vinyl cyclopropane | 57% | 73% e.e. | 11:1 |
| Example 11 | phenyl-CH=N, CO$_2$Et, vinyl cyclopropane | 63% | 73% e.e. | 10:1 |
| Example 12 | phenyl-CH=N, CO$_2$Et, vinyl cyclopropane | 62% | 67% e.e. | 8.4:1 |

TABLE 7

| | Optically active compound (3) | Yield | Optical purity | Optically active compound (3): 7-membered ring compound (7) |
|---|---|---|---|---|
| Example 13 | phenyl-CH=N, CO$_2$Et, vinyl cyclopropane | 55% | 51% e.e. | 6.7:1 |

TABLE 7-continued

| | Optically active compound (3) | Yield | Optical purity | Optically active compound (3): 7-membered ring compound (7) |
|---|---|---|---|---|
| Example 14 | | 51% | 46% e.e | 5.8:1 |
| Example 15 | | 42% | 7% e.e. | 5.8:1 |
| Example 16 | | 34% | 5% e.e. | 5.3:1 |
| Example 17 | | 59% | 50% e.e. | 6.7:1 |
| Example 18 | | 60% | 68% e.e. | 8.6:1 |
| Example 19 | | 43% | 24% e.e. | 4.2:1 |
| Example 20 | | 61% | 65% e.e. | 15:1 |

TABLE 8

| | Optically active compound (3) | Yield | Optical purity | Optically active compound (3): 7-membered ring compound (7) |
|---|---|---|---|---|
| Comparative Example 1 | [structure: benzylidene-N, CO₂Et cyclopropane with vinyl] and enantiomer thereof | 35% | 0% e.e. (Racemic compound) | 2.9:1 |
| Comparative Example 2 | [structure: benzylidene-N, CO₂Et cyclopropane with vinyl] and enantiomer thereof | 29% | 0% e.e. (Racemic compound) | 6:1 |
| Comparative Example 3 | [structure: benzylidene-N, CO₂Et cyclopropane with vinyl] and enantiomer thereof | 40% | 0% e.e. (Racemic compound) | 3.8:1 |

Example 21

The toluene solution (0.95 g) of (E)-N-phenylmethyleneglycine ethyl ester (pure (E)-N-phenylmethyleneglycine ethyl ester: 0.49 g, 2.57 mmol) obtained in the same manner as in Synthesis Example 1 and toluene (20 mL) were mixed, and (E)-1,4-dibromo-2-butene (0.50 g, 2.34 mmol) and (8S,9R)-(−)-N-benzylcinchonidinium chloride (0.099 g, 0.23 mmol, 10 mol %) were added thereto at room temperature. The obtained mixture was cooled to 0° C. and an aqueous 50% potassium hydroxide solution (4 mL) was added dropwise thereto, followed by a reaction at 0° C. for 23 hours. After completion of the reaction, water (2 mL) was added to the obtained mixture and stirring was stopped to perform liquid separation. The obtained organic layer was washed with an aqueous 10% ammonium chloride solution (2 mL) to obtain a solution containing (1S,2R)-1-(N-phenylmethylene)amino-2-vinylcyclopropanecarboxylic acid ethyl ester.

The content of (1S,2R)-1-(N-phenylmethylene)amino-2-vinylcyclopropanecarboxylic acid ethyl ester was measured by quantitative analysis of this solution under the same conditions as in Example 1 to determine a yield. Yield: 66%. (1S,2R)-1-(N-phenylmethylene)amino-2-vinylcyclopropanecarboxylic acid ethyl ester:ethyl 7-phenyl-6,7-dihydro-1H-azepine-2-carboxylate=7.5:1. A diastereomer of (1S,2R)-1-(N-phenylmethylene)amino-2-vinylcyclopropanecarboxylic acid ethyl ester was not detected from the solution containing (1S,2R)-1-(N-phenylmethylene)amino-2-vinylcyclopropanecarboxylic acid ethyl ester.

An aqueous 1M hydrochloric acid (2 mL) was added to the obtained solution and the obtained mixture was subjected to imine-hydrolysis by stirring at room temperature for 1.5 hours. After completion of the imine-hydrolysis, the aqueous layer was separated from the obtained mixture and the organic layer was extracted by adding water (2 mL). The aqueous layer obtained after extraction and the previously separated aqueous layer were combined to obtain an aqueous solution containing (1S,2R)-1-amino-2-vinylcyclopropanecarboxylic acid ethyl ester hydrochloride.

The optical purity of (1S,2R)-1-amino-2-vinylcyclopropanecarboxylic acid ethyl ester hydrochloride was measured by the analysis under the same conditions as in Example 1. Optical purity: 3% e.e.

Example 22

In the same manner as in Example 1, except that (E)-1,4-dichloro-2-butene was used in place of (E)-1,4-dibromo-2-butene and the reaction was carried out for 15 hours in Example 1, a solution containing (1S,2R)-1-(N-phenylmethylene)amino-2-vinylcyclopropanecarboxylic acid ethyl ester was obtained.

Yield: 50%. Optical purity: 74% e.e. (1S,2R)-1-(N-phenylmethylene)amino-2-vinylcyclopropanecarboxylic acid ethyl ester:ethyl 7-phenyl-6,7-dihydro-1H-azepine-2-carboxylate=5.2:1.

A diastereomer of (1S,2R)-1-(N-phenylmethylene)amino-2-vinylcyclopropanecarboxylic acid ethyl ester was not detected from a solution containing (1S,2R)-1-(N-phenylmethylene)amino-2-vinylcyclopropanecarboxylic acid ethyl ester.

Example 23

Production of (1S,2R)-1-amino-2-vinylcyclopropanecarboxylic acid ethyl ester

The toluene solution (131.5 g) of (E)-N-phenylmethyleneglycine ethyl ester (pure (E)-N-phenylmethyleneglycine ethyl ester: 65.7 g, 343.6 mmol) obtained in the same manner as in Synthesis Example 1 and toluene (490 mL) were mixed, and (E)-1,4-dibromo-2-butene (70.0 g, 327.3 mmol) and (R)-2,10-di-t-butyl-3,9-dimethoxy-6-methyl-6-(1-naphthalen-1-ylethyl)-4,8-bis(3,5-bistrifluoromethylphenyl)-6,7-dihydro-5H-dibenzo[c,e]-azepinium bromide (1.02 g, 0.98 mmol) were added thereto at room temperature. The obtained mixture was cooled to 0° C. and an aqueous 50% potassium hydroxide solution (367 g) (potassium hydroxide: 3273 mmol) was added dropwise thereto over 3.5 hours, followed by a reaction at 0° C. for 38.5 hours. After completion of the reaction, water (210 mL) was added to the obtained mixture and then liquid separation was carried out. The obtained organic layer was washed with an aqueous 10% ammonium chloride solution (140 g) to obtain a solution containing (1S,2R)-1-(N-phenylmethylene)amino-2-vinylcyclopropanecarboxylic acid ethyl ester.

The content of (1S,2R)-1-(N-phenylmethylene)amino-2-vinylcyclopropanecarboxylic acid ethyl ester was measured by quantitative analysis of this solution under the same conditions as in Example 1 to determine a yield. Yield: 63%. (1S,2R)-1-(N-phenylmethylene)amino-2-vinylcyclopropanecarboxylic acid ethyl ester:ethyl 7-phenyl-6,7-dihydro-1H-azepine-2-carboxylate=9.5:1. A diastereomer of (1S,2R)-1-(N-phenylmethylene)amino-2-vinylcyclopropanecarboxylic acid ethyl ester was not detected from a solution containing (1S,2R)-1-(N-phenylmethylene)amino-2-vinylcyclopropanecarboxylic acid ethyl ester.

Water (95 mL) was poured into the obtained solution and an aqueous 35% hydrochloric acid solution (34.1 g) was added, and then imine-hydrolysis was carried out by stirring at room temperature for 2 hours. After completion of the imine-hydrolysis, the aqueous layer was separated and the organic layer was extracted by adding water (70 mL). The aqueous layer obtained by extraction and the previously separated aqueous layer were combined to obtain (1S,2R)-1-amino-2-vinylcyclopropanecarboxylic acid ethyl ester hydrochloride as an aqueous solution. The optical purity was determined by analyzing the obtained aqueous solution under the same conditions as in Example 1. Optical purity: 73% e.e.

Example 24

Production of (1R,2S)-1-amino-2-vinylcyclopropanecarboxylic acid ethyl ester hemisulfate The toluene solution (68.3 g) of (E)-N-phenylmethyleneglycine ethyl ester (pure N-phenylmethyleneglycine ethyl ester: 32.5 g, 170 mmol) obtained in the same manner as in Synthesis Example 1 and toluene (484 mL) were mixed, and (E)-1,4-dibromo-2-butene (69.1 g, 323 mmol) and (S)-2,10-di-t-butyl-3,9-dimethoxy-6-methyl-6-(1-naphthalen-1-ylethyl)-4,8-bis(3,5-bistrifluoromethylphenyl)-6,7-dihydro-5H-dibenzo[c,e]-azepinium bromide (1.01 g, 0.97 mmol) were added thereto at room temperature. The obtained mixture was cooled to 0° C. and an aqueous 50% potassium hydroxide solution (362 g) (potassium hydroxide: 3230 mmol) was added dropwise thereto over 1 hour, followed by a reaction at 0° C. for 2 hours. A toluene solution (68.3 g) of (E)-N-phenylmethyleneglycine ethyl ester (pure N-phenylmethyleneglycine ethyl ester: 32.5 g, 170 mmol) was added dropwise thereto at 0° C. over 1.5 hours, and then reaction was continued at 0° C. for 13.5 hours. After completion of the reaction, water (205 mL) was added to the obtained mixture, and then the organic layer was obtained by liquid separation of the aqueous layer. The organic layer was washed by pouring an aqueous 20% sodium chloride solution (138 g) to obtain a solution containing (1R,2S)-1-(N-phenylmethylene)amino-2-vinylcyclopropanecarboxylic acid ethyl ester.

The content of (1R,2S)-1-(N-phenylmethylene)amino-2-vinylcyclopropanecarboxylic acid ethyl ester was measured by quantitative analysis of the obtained solution under the same conditions as in Example 1 to determine a yield. Yield: 61%. (1R,2S)-1-(N-phenylmethylene)amino-2-vinylcyclopropanecarboxylic acid ethyl ester:ethyl 7-phenyl-6,7-dihydro-1H-azepine-2-carboxylate=7.9:1. A diastereomer of (1S,2R)-1-(N-phenylmethylene)amino-2-vinylcyclopropanecarboxylic acid ethyl ester was not detected from a solution containing the (1R,2S)-1-(N phenylmethylene)amino-2-vinylcyclopropanecarboxylic acid ethyl ester.

Subsequently, water (93 mL) was poured into the obtained solution at room temperature, and then an aqueous 35% hydrochloric acid solution (32.0 g) was added dropwise at room temperature over 1 hour and imine-hydrolysis was carried out at room temperature for 2 hours. After completion of the imine-hydrolysis, the aqueous layer was separated and then the organic layer was extracted by pouring an aqueous 0.5% hydrochloric acid solution (58.8 g) at room temperature. The aqueous layer obtained by extraction and the previously separated aqueous layer were combined to obtain (1R,2S)-1-amino-2-vinylcyclopropanecarboxylic acid ethyl ester hydrochloride as an aqueous solution (235 g). Yield: 60% (overall yield from 1,4-dibromo-2-butene). The optical purity was determined by analyzing the obtained aqueous solution under the same conditions as in Example 1. Optical purity: 71% e.e.

From the obtained aqueous (1R,2S)-1-amino-2-vinylcyclopropanecarboxylic acid ethyl ester hydrochloride solution (235 g), 46.6 g ((1R,2S)-1-amino-2-vinylcyclopropanecarboxylic acid ethyl ester hydrochloride: 6.0 g, 38.7 mmol) was separated and toluene (40 mL) was poured into the separated aqueous solution. This mixture was cooled in an ice bath and the mixture was neutralized by adding dropwise an aqueous 48% sodium hydroxide solution (4.68 g). After completion of the neutralization, the organic layer was separated and the obtained aqueous layer was extracted by pouring toluene (20 mL). The organic layer obtained by extraction and the previously separated organic layer were combined, dried over magnesium sulfate, and then a mixture of sulfuric acid (1.9 g, 19.3 mmol), ethanol (10 mL) and toluene (10 mL) was added dropwise to the organic layer at room temperature over 1 hour. The obtained mixture (106.7 g) was concentrated under reduced pressure to 38.7 g and then ethanol (4.6 g) was poured into the concentrated residue thereby adjusting the solvent composition of the mixture to toluene:ethanol=8:1 (weight ratio). In this mixture, (1R,2S)-1-amino-2-vinylcyclopropanecarboxylic acid ethyl ester hemisulfate having a low optical purity was crystallized and the obtained crystals were isolated by filtration to obtain a solution containing (1R,2S)-1-amino-2-vinylcyclopropanecarboxylic acid ethyl ester hemisulfate having a high optical purity. Overall yield from (E)-1,4-dibromo-2-butene: 40%. Optical purity: 94.5% e.e.

Overall yield of crystal isolated by filtration: 18%. Optical purity: 14% e.e.

(1R,2S)-1-amino-2-vinylcyclopropanecarboxylic acid ethyl ester hemisulfate $^1$H-NMR (CD$_3$OD, 400 MHz) δ ppm: 5.88-5.75 (1H, m), 5.38 (1H, dd, J=1.5, 17.1 Hz), 5.17 (1H, dd, J=1.5, 10.3 Hz), 4.26 (2H, q, J=6.8 Hz), 2.56-2.47 (1H, m), 1.86 (1H, dd, J=6.4, 10.2 Hz), 1.70 (1H, dd, J=6.4, 8.3 Hz), 1.30 (3H, t, J=6.8 Hz)

$^{13}$C-NMR (CD$_3$OD, 400 MHz) δ ppm: 169.0, 133.3, 119.6, 63.5, 41.2, 31.6, 20.0, 14.5

Example 25

Production of (1R,2S)-1-amino-2-vinylcyclopropanecarboxylic acid ethyl ester 4-chlorobenzoate The solution (246 g) containing (1R,2S)-1-amino-2-vinylcyclopropanecarboxylic acid ethyl ester hemisulfate having an optical purity of 94% e.e. (pure (1R,2S)-1-amino-2-vinylcyclopropanecarboxylic acid ethyl ester hemisulfate: 16.1 g, 78.9 mmol) obtained in the same manner as in Example 24 and water (82 g) were mixed, and an aqueous 48% sodium hydroxide solution (3.42 g) was added thereto at 5° C. and then the obtained mixture was heated to room temperature to perform liquid separation. The obtained organic layer was dehydrated over magnesium sulfate and then 4-chlorobenzoic acid (11.8 g, 75.6 mmol) was added thereto at room temperature. After stirring the obtained mixture for 30 minutes, the solvent (152 g) was distilled off by concentrating the mixture under reduced pressure. The thus obtained slurry was stirred at room temperature for 1 hour, refrigerated at 3° C. for 2 days and then filtered at 5° C. to obtain crystals. The crystals were washed with toluene (12 g) and then dried under reduced pressure to obtain (1R,2S)-1-amino-2-vinylcyclopropanecarboxylic acid ethyl ester 4-chlorobenzoate (17.7 g, 56.7 mmol). Yield: 72%. The optical purity of the obtained (1R, 2S)-1-amino-2-vinylcyclopropanecarboxylic acid ethyl ester 4-chlorobenzoate was determined by analyzing under the same conditions as in Example 1. Optical purity: more than 99% e.e.

Example 26

Production of (1R,2S)-1-amino-2-vinylcyclopropanecarboxylic acid ethyl ester hemisulfate Tetrahydrofuran (80 g) was poured into (1R,2S)-1-amino-2-vinylcyclopropanecarboxylic acid ethyl ester 4-chlorobenzoate (8.0 g, 25.7 mmol) obtained in Example 25. After stirring, a mixed liquid of 96% sulfuric acid (1.31 g, 12.8 mmol) and tetrahydrofuran (80 g) was added dropwise over 2.5 hours. The obtained mixture was stirred at room temperature for 1 hour, cooled to 1° C. over 2.5 hours and then filtered at the same temperature to obtain a solid. The obtained solid was washed with a mixed liquid of tetrahydrofuran (8 g) and toluene (4 g) and then dried under reduced pressure to obtain (1R,2S)-1-amino-2-vinylcyclopropanecarboxylic acid ethyl ester hemisulfate having an optical purity of more than 99% e.e. (3.98 g, 19.5 mmol). Yield: 76%.

INDUSTRIAL APPLICABILITY

An optically active 1-amino-2-vinylcyclopropanecarboxylic acid ester is useful, for example, as an intermediate for synthesis of medicines such as an antiviral agent.

The present invention is useful in the production of medicines since it provides a method for producing an optically active 1-N-(arylenemethylene)amino-2-vinylcyclopropanecarboxylic acid ester represented by formula (3), and a method for producing an optically active 1-amino-2-vinylcyclopropanecarboxylic acid ester from the compound.

The invention claimed is:

1. A method for producing an optically active 1-N-(arylmethylene)amino-2-vinylcyclopropanecarboxylic acid ester represented by formula (3)

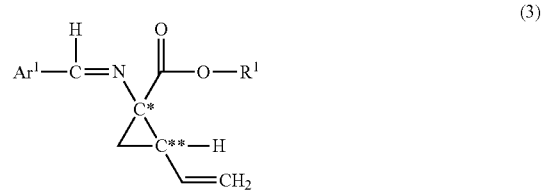

(wherein Ar$^1$ and R$^1$ are as defined below, C* and C represent an asymmetric carbon atom, C is an S-configuration when C* is an R-configuration, and C** is an R-configuration when C* is an S-configuration), the method comprising a step of reacting an N-(arylmethylene)glycine ester represented by formula (1)

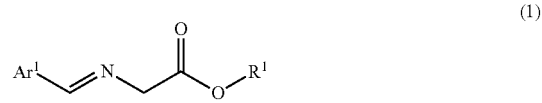

(wherein Ar$^1$ represents an aromatic group, and R$^1$ represents an alkyl group having 1 to 12 carbon atoms or an alkenyl group having 2 to 12 carbon atoms), with a compound represented formula (2)

(wherein Y$^1$ and Y$^2$ each independently represents a halogen atom, an alkanesulfonyloxy group having 1 to 6 carbon atoms, a perfluoroalkanesulfonyloxy group having 1 to 6 carbon atoms or a benzenesulfonyloxy group, in which one or more hydrogen atoms contained in the benzenesulfonyloxy group, each independently may be substituted with an alkyl group having 1 to 6 carbon atoms, a halogen atom or a nitro group), in the presence of a base and an optically active quaternary ammonium salt.

2. The method according to claim 1, wherein $Ar^1$ is a phenyl group which is optionally substituted with one or more selected from the group consisting of an alkyl group having 1 to 12 carbon atoms, an alkoxy group having 1 to 12 carbon atoms, a halogen atom, a nitro group, a cyano group and a trifluoromethyl group.

3. The method according to claim 1, wherein $Ar^1$ is a phenyl group or a 4-chlorophenyl group.

4. The method according to claim 1, wherein $R^1$ is an alkyl group having 1 to 12 carbon atoms.

5. The method according to claim 1, wherein the reaction of the N-(arylmethylene)glycine ester represented by formula (1) with the compound represented by formula (2) is carried, out using water and an aromatic solvent or an ether solvent.

6. The method according to claim 1, wherein the optically active quaternary ammonium salt is a compound represented by formula (5)

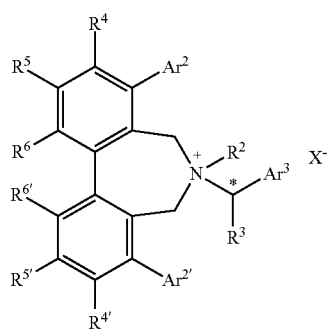

(5)

(wherein $Ar^2$ and $Ar^{2'}$ each independently represents an optionally substituted phenyl group, $Ar^3$ represents an optionally substituted aromatic hydrocarbon group, a substituted straight-chain hydrocarbon group having 1 to 12 carbon atoms, or an optionally substituted branched or cyclic aliphatic hydrocarbon group having 3 to 12 carbon atoms, $R^2$ represents an optionally substituted aliphatic hydrocarbon group having 1 to 12 carbon atoms, $R^3$ represents a straight-chain hydrocarbon group having 1 to 12 carbon atoms, or $R^2$ and $R^3$ are combined to form an alkylene group having 2 to 6 carbon atoms, $R^4$, $R^{4'}$, $R^5$, $R^{5'}$, $R^6$ and $R^{6'}$, each independently represents a hydrogen atom, an aliphatic hydrocarbon group having 1 to 12 carbon atoms or an alkoxy group having 1 to 12 carbon atoms, * represents an asymmetric carbon atom, and $X^-$ represents a monovalent anion).

7. The method according to claim 6, wherein $Ar^2$ and $Ar^{2'}$ each independently represents a 3,4,5-trifluorophenyl group or a 3,5-bis(trifluoromethyl)phenyl group, $R^2$ and $R^3$ each independently represents an alkyl group having 1 to 12 carbon atoms, and $Ar^3$ represents a phenyl group or a naphthyl group.

8. The method according to claim 1, wherein the optically active quaternary ammonium salt is a compound represented by formula (6)

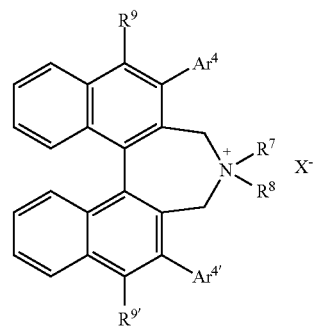

(6)

(wherein $Ar^4$ and $Ar^{4'}$ each independently represents an optionally substituted phenyl group, $R^7$ and $R^8$ each independently represents an aliphatic hydrocarbon group having 1 to 12 carbon atoms, $R^9$ and $R^{9'}$ each independently represents a hydrogen atom, an aliphatic hydrocarbon group having 1 to 12 carbon atoms or an alkoxy group having 1 to 12 carbon atoms, and $X^-$ represents a monovalent anion).

9. An optically active 1-N-(arylmethylene)amino-2-vinylcyclopropanecarboxylic acid ester represented by formula (3):

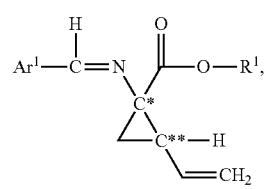

(3)

wherein the optically active 1-N-(arylmethylene)amino-2-vinylcyclopropanecarboxylic acid ester has an enantiomeric excess of at least about 40%, (wherein $Ar^1$ represents an aromatic group, $R^1$ represents an alkyl group having 1 to 12 carbon atoms or an alkenyl group having 2 to 12 carbon atoms, and C* and C represent an asymmetric carbon atom, C is an S-configuration when C* is an R-configuration, and C** is an R-configuration when C* is an S-configuration).

10. The 1-N-(arylmethylene)amino-2-vinylcyclopropanecarboxylic acid ester according to claim 9, wherein $R^1$ is an alkyl group having 1 to 12 carbon atoms and $Ar^1$ is a phenyl group or a 4-chlorophenyl group.

11. A method for producing an optically active 1-amino-2-vinylcyclopropanecarboxylic acid ester represented by formula (4)

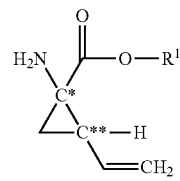

(4)

(wherein $R^1$, C* and C** are as defined below), the method comprising a step of subjecting an optically active 1-N-(arylmethylene)amino-2-vinylcyclopropanecarboxylic acid ester represented by formula (3)

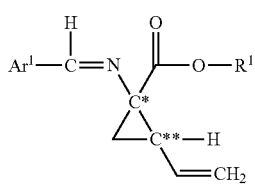

(3)

(wherein Ar¹ and R¹ are as defined below, C* and C represent an asymmetric carbon atom, C is an S-configuration when C* is an R-configuration, and C** is an R-configuration when C* is an S-configuration) to imine-hydrolysis, which is obtained by reacting an N-(arylmethylene)glycine ester represented by formula (1)

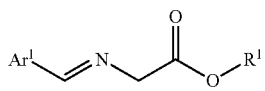

(1)

(wherein Ar¹ represents an aromatic group and R¹ represents an alkyl group having 1 to 12 carbon atoms or an alkenyl group having 2 to 12 carbon atoms), with a compound represented by formula (2)

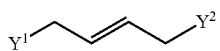

(2)

(wherein Y¹ and Y² each independently represents a halogen atom, an alkanesulfonyloxy group having 1 to 6 carbon atoms, a perfluoroalkanesulfonyloxy group having 1 to 6 carbon atoms or a benzenesulfonyloxy group, in which one or more hydrogen atoms contained in the benzenesulfonyloxy group each independently is optionally substituted with an alkyl group having 1 to 6 carbon atoms, a halogen atom or a nitro group), in the presence of a base and an optically active quaternary ammonium salt.

12. A method for producing, an optically active 1-amino-2-vinylcyclopropanecarboxylic acid ester represented by formula (4)

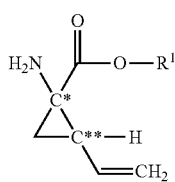

(4)

(wherein R¹, C* and C** are as defined below), the method comprising steps of subjecting an optically active 1-N-(arylmethylene)amino-2-vinylcyclopropanecarboxylic acid ester represented by formula (3)

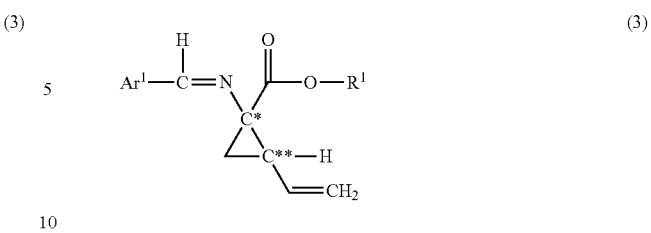

(3)

(wherein Ar¹ and R¹ are as defined below, C* and C represent an asymmetric carbon atom, C is an S-configuration when C* is an R-configuration, and C** is an R-configuration when C* is an S-configuration) to imine-hydrolysis, which is obtained by reacting an N-(arylmethylene)glycine ester represented by formula (1)

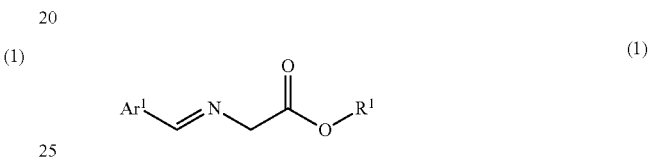

(1)

(wherein Ar¹ represents an aromatic group and R¹ represents an alkyl group having 1 to 12 carbon atoms or an alkenyl group having 2 to 12 carbon atoms), with a compound represented by formula (2)

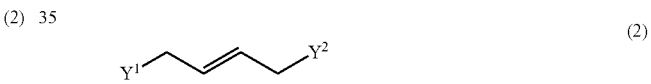

(2)

(wherein Y¹ and Y² each independently represents a halogen atom, an alkanesulfonyloxy group having 1 to 6 carbon atoms, a perfluoroalkanesulfonyloxy group having 1 to 6 carbon atoms or a benzenesulfonyloxy group, in which one or more hydrogen atoms contained in the benzenesulfonyloxy group each independently is optionally substituted with an alkyl group having 1 to 6 carbon atoms, a halogen atom or a intro group), in the presence of a base and an optically active quaternary ammonium salt; and forming a salt of the product obtained by imine-hydrolysis, and an achiral acid, and purifying, the salt.

13. The method according to claim 12, wherein the achiral acid is sulfuric acid or a halogen-substituted benzoic acid.

14. The method according to claim 12, wherein the step of purifying the salt is a step of forming a salt of the product obtained by imine-hydrolysis and sulfuric acid in a solvent, precipitating a salt having a low optical purity, obtaining the salt dissolved in the solvent, isolating a 1-amino-2-vinylcyclopropanecarboxylic acid ester from the obtained salt, forming a salt of the isolated 1-amino-2-vinylcyclopropanecarboxylic acid ester and a halogen-substituted benzoic acid, and recrystallizing the salt.

15. A method for improving an optical purity of an optically active 1-amino-2-vinylcyclopropanecarboxylic acid ester by deriving an optically active 1-amino-2-vinylcyclopropanecarboxylic acid ester represented by formula (4)

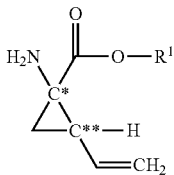

(4)

(wherein R¹ represents an alkyl group having 1 to 12 carbon atoms or an alkenyl group having 2 to 12 carbon atoms, C* and C represent an asymmetric carbon atom, C is an S-configuration when C* is an R-configuration, and C** is an R-configuration when C* is an S-configuration), to a salt with an achiral acid, and purifying the salt.

16. The method according to claim 15, wherein achiral acid is sulfuric acid or a halogen-substituted benzoic acid.

17. The method according to claim 15, which comprises forming a salt of an optically active 1-amino-2-vinylcyclopropanecarboxylic acid ester represented by formula (4) and sulfuric acid in a solvent, precipitating a salt having a low optical purity, obtaining the salt dissolved in the solvent, isolating a 1-amino-2-vinylcyclopropanecarboxylic acid ester from the obtained salt, forming, a salt of the isolated 1-amino-2-vinylcyclopropanecarboxylic acid ester and a halogen-substituted benzoic acid, and recrystallizing the salt.

18. A salt of an optically active 1-amino-2-vinylcyclopropanecarboxylic acid ester represented by formula (4)

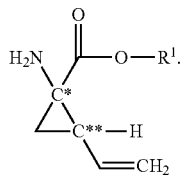

(4)

(wherein R¹ represents an alkyl group having 1 to 12 carbon atoms or an alkenyl group having 2 to 12 carbon atoms, C* and C represent an asymmetric carbon atom, C is an S-configuration when C* is an R-configuration, and C** is an R-configuration when C* is an S-configuration), and a halogen-substituted benzoic acid.

19. The salt according to claim 18, wherein R¹ is an alkyl group having 1 to 12 carbon atoms and the halogen-substituted benzoic acid is 4-chlorobenzoic acid.

* * * * *